(12) United States Patent
Harris et al.

(10) Patent No.: US 11,992,212 B2
(45) Date of Patent: May 28, 2024

(54) SURGICAL STAPLING END EFFECTOR COMPONENT WITH TIP HAVING VARYING BEND ANGLE

(71) Applicant: Cilag GmbH International, Zug (CH)

(72) Inventors: Jason L. Harris, Lebanon, OH (US); Gregory J. Bakos, Mason, OH (US); Chester O. Baxter, III, Loveland, OH (US); Frederick E. Shelton, IV, Hillsboro, OH (US); Hilary A. Reinhardt, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/079,144

(22) Filed: Dec. 12, 2022

(65) Prior Publication Data

US 2023/0255628 A1 Aug. 17, 2023

Related U.S. Application Data

(63) Continuation of application No. 16/035,856, filed on Jul. 16, 2018, now Pat. No. 11,564,684, which is a
(Continued)

(51) Int. Cl.
*A61B 17/072* (2006.01)
*A61B 17/28* (2006.01)
(Continued)

(52) U.S. Cl.
CPC ...... *A61B 17/072* (2013.01); *A61B 17/07207* (2013.01); *A61B 17/282* (2013.01);
(Continued)

(58) Field of Classification Search
CPC .................. A61B 17/072; A61B 2090/0807
See application file for complete search history.

(56) References Cited

U.S. PATENT DOCUMENTS

| 4,805,823 A | 2/1989 | Rothfuss |
| 5,014,899 A | 5/1991 | Presty et al. |
| (Continued) | | |

FOREIGN PATENT DOCUMENTS

| CN | 104720859 A | 6/2015 |
| CN | 110520065 A | 11/2019 |
| (Continued) | | |

OTHER PUBLICATIONS

Brazilian Search Report from Brazilian Patent Application No. 112021000554, dated May 15, 2023, 4 pages.
(Continued)

*Primary Examiner* — Chelsea E Stinson
(74) *Attorney, Agent, or Firm* — Lempia Summerfield Katz LLC

(57) ABSTRACT

A surgical instrument, operable to compress, staple, and cut tissue, includes a body, a shaft, and an end effector with a pair of jaws. A placement tip that is bent, angled, or curved and extends distally from one of the jaws of the end effector. The placement tip is elastically deformable when the placement tip is subject to a clamping force, such as when the end effector is closed with the jaws in contact or when tissue is clamped between the jaws of the end effector. When the placement tip deflects, relative angles defined in part by the placement tip vary compared to an initial state without the clamping force. Furthermore, a distal end of the placement tip may change position based on the state of deflection of the placement tip in response to the clamping force.

25 Claims, 24 Drawing Sheets

Related U.S. Application Data continuation-in-part of application No. 15/435,573, filed on Feb. 17, 2017, now Pat. No. 10,828,031.

(51) Int. Cl.
*A61B 17/29* (2006.01)
*A61B 17/00* (2006.01)
*A61B 17/064* (2006.01)

(52) U.S. Cl.
CPC .. *A61B 17/2909* (2013.01); *A61B 2017/0046* (2013.01); *A61B 2017/00473* (2013.01); *A61B 2017/00964* (2013.01); *A61B 2017/0645* (2013.01); *A61B 2017/07221* (2013.01); *A61B 2017/07257* (2013.01); *A61B 2017/07271* (2013.01); *A61B 2017/07285* (2013.01); *A61B 2017/2913* (2013.01); *A61B 2017/2926* (2013.01); *A61B 2017/2946* (2013.01)

(56) References Cited

U.S. PATENT DOCUMENTS

| | | |
|---|---|---|
| 5,415,334 A | 5/1995 | Williamson, IV et al. |
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,752,965 A | 5/1998 | Francis et al. |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 6,939,358 B2 | 9/2005 | Palacios et al. |
| 6,978,921 B2 | 12/2005 | Shelton, IV et al. |
| 7,000,818 B2 | 2/2006 | Shelton, IV et al. |
| 7,143,923 B2 | 12/2006 | Shelton, IV et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,524,320 B2 | 4/2009 | Tierney et al. |
| 7,644,848 B2 | 1/2010 | Swayze et al. |
| 7,691,098 B2 | 4/2010 | Wallace et al. |
| 7,721,930 B2 | 5/2010 | Mckenna et al. |
| 7,806,891 B2 | 10/2010 | Nowlin et al. |
| 8,066,166 B2 | 11/2011 | Demmy et al. |
| 8,136,711 B2 | 3/2012 | Beardsley et al. |
| 8,210,411 B2 | 7/2012 | Yates et al. |
| 8,348,123 B2 | 1/2013 | Scirica et al. |
| 8,371,491 B2 | 2/2013 | Huitema et al. |
| 8,403,195 B2 | 3/2013 | Beardsley et al. |
| 8,403,196 B2 | 3/2013 | Beardsley et al. |
| 8,408,439 B2 | 4/2013 | Huang et al. |
| 8,453,904 B2 | 6/2013 | Eskaros et al. |
| 8,453,914 B2 | 6/2013 | Laurent et al. |
| 8,479,969 B2 | 7/2013 | Shelton, IV |
| 8,496,153 B2 | 7/2013 | Demmy et al. |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,690,039 B2 | 4/2014 | Beardsley et al. |
| 8,714,429 B2 | 5/2014 | Demmy |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,844,790 B2 | 9/2014 | Demmy et al. |
| 9,016,546 B2 | 4/2015 | Demmy et al. |
| 9,039,736 B2 | 5/2015 | Scirica et al. |
| 9,186,142 B2 | 11/2015 | Fanelli et al. |
| 9,301,759 B2 | 4/2016 | Spivey et al. |
| 9,433,416 B2 | 9/2016 | Beardsley et al. |
| 9,517,065 B2 | 12/2016 | Simms et al. |
| 9,522,004 B2 | 12/2016 | Demmy |
| 9,572,574 B2 | 2/2017 | Shelton, IV et al. |
| 9,597,078 B2 | 3/2017 | Scirica et al. |
| 9,622,746 B2 | 4/2017 | Simms et al. |
| 9,713,470 B2 | 7/2017 | Scirica et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,420 B2 | 12/2017 | Shelton, IV et al. |
| 9,839,421 B2 | 12/2017 | Zerkle et al. |
| 9,913,642 B2 | 3/2018 | Leimbach et al. |
| 9,936,952 B2 | 4/2018 | Demmy |
| 9,936,968 B2 | 4/2018 | Demmy et al. |
| 9,943,311 B2 | 4/2018 | Scirica et al. |
| 10,080,564 B2 | 9/2018 | Beardsley et al. |
| 10,111,660 B2 | 10/2018 | Hemmann |
| D833,010 S | 11/2018 | Harris et al. |
| 10,166,023 B2 | 1/2019 | Vendely et al. |
| 10,349,939 B2 | 7/2019 | Shelton, IV et al. |
| 10,349,940 B2 | 7/2019 | Zeiner et al. |
| 10,433,863 B2 | 10/2019 | Glutz et al. |
| 10,729,434 B2* | 8/2020 | Harris .............. A61B 17/07207 |
| 10,828,031 B2* | 11/2020 | Harris .............. A61B 17/07207 |
| 10,912,561 B2* | 2/2021 | Harris .............. A61B 17/07292 |
| 10,973,515 B2* | 4/2021 | Harris ................ A61B 17/072 |
| 11,090,048 B2* | 8/2021 | Fanelli .............. A61B 17/0644 |
| 11,154,296 B2* | 10/2021 | Aronhalt .......... A61B 17/00491 |
| 11,179,154 B2* | 11/2021 | Harris .............. A61B 17/07207 |
| 11,197,670 B2* | 12/2021 | Shelton, IV ........ H01M 10/425 |
| 11,272,930 B2* | 3/2022 | Harris ................ A61B 17/2909 |
| 2004/0243151 A1 | 12/2004 | Demmy et al. |
| 2005/0070929 A1 | 3/2005 | Dalessandro et al. |
| 2005/0216055 A1 | 9/2005 | Scirica et al. |
| 2009/0095791 A1 | 4/2009 | Eskaros et al. |
| 2010/0094315 A1 | 4/2010 | Beardsley et al. |
| 2011/0186614 A1 | 8/2011 | Kasvikis |
| 2012/0143218 A1 | 6/2012 | Beardsley et al. |
| 2012/0241497 A1 | 9/2012 | Mandakolathur et al. |
| 2012/0289979 A1 | 11/2012 | Eskaros et al. |
| 2013/0068818 A1 | 3/2013 | Kasvikis |
| 2013/0172929 A1 | 7/2013 | Hess et al. |
| 2013/0334280 A1 | 12/2013 | Krehel et al. |
| 2014/0166723 A1 | 6/2014 | Beardsley et al. |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239041 A1 | 8/2014 | Zerkle et al. |
| 2014/0239042 A1 | 8/2014 | Simms et al. |
| 2014/0239043 A1 | 8/2014 | Simms et al. |
| 2014/0239044 A1 | 8/2014 | Hoffman |
| 2014/0276736 A1 | 9/2014 | Worrell et al. |
| 2015/0173752 A1 | 6/2015 | Demmy et al. |
| 2015/0216528 A1 | 8/2015 | Demmy |
| 2015/0282809 A1 | 10/2015 | Shelton, IV et al. |
| 2015/0374373 A1 | 12/2015 | Rector et al. |
| 2016/0143659 A1 | 5/2016 | Glutz et al. |
| 2016/0278774 A1 | 9/2016 | Shelton, IV et al. |
| 2016/0338703 A1 | 11/2016 | Scirica et al. |
| 2017/0055981 A1 | 3/2017 | Vendely et al. |
| 2017/0086823 A1 | 3/2017 | Leimbach et al. |
| 2017/0156725 A1 | 6/2017 | Hemmann |
| 2018/0235609 A1 | 8/2018 | Harris et al. |
| 2018/0235610 A1 | 8/2018 | Harris et al. |
| 2018/0235611 A1 | 8/2018 | Harris et al. |
| 2018/0235619 A1 | 8/2018 | Harris et al. |
| 2018/0325514 A1 | 11/2018 | Harris et al. |
| 2018/0325515 A1 | 11/2018 | Harris et al. |
| 2018/0325516 A1 | 11/2018 | Harris et al. |
| 2019/0000481 A1 | 1/2019 | Harris et al. |
| 2019/0076143 A1* | 3/2019 | Smith .............. A61B 17/07207 |
| 2019/0175173 A1 | 6/2019 | Harris et al. |

(56) References Cited

U.S. PATENT DOCUMENTS

FOREIGN PATENT DOCUMENTS

| EP | 2772202 A2 | 9/2014 |
|---|---|---|
| EP | 2772203 A2 | 9/2014 |
| EP | 2913010 A2 | 9/2015 |
| EP | 3363390 A2 | 8/2018 |
| JP | 2009189839 A | 8/2009 |
| JP | 2011072791 A | 4/2011 |
| JP | 2013542005 A | 11/2013 |
| JP | 2014171909 A | 9/2014 |
| JP | 2014198249 A | 10/2014 |
| JP | 2014531262 A | 11/2014 |
| JP | 2015513978 A | 5/2015 |
| JP | 2015144807 A | 8/2015 |
| JP | 2016508791 A | 3/2016 |
| JP | 2017099878 A | 6/2017 |
| WO | 2004096057 A2 | 11/2004 |
| WO | 2013151888 A1 | 10/2013 |
| WO | 2017083129 A1 | 5/2017 |

OTHER PUBLICATIONS

Brazilian Search Report from Brazilian Patent Application No. 112021000557, dated May 15, 2023, 4 pages.
Brazilian Search Report from Brazilian Patent Application No. 112021000654, dated May 15, 2023, 4 pages.
Declaration of Non-Establishment of International Search Report and Written Opinion dated Dec. 13, 2019 for Application PCT/IB2019/055964, 6 pgs.
English translation of Notification of Reasons for Refusal in Japanese Patent Application No. 2021-502601, dated Apr. 18, 2023, 7 pages.
English translation of Notification of Reasons for Refusal in Japanese Patent Application No. 2021502401, dated May 2, 2023, 7 pages.
European Search Report and Written Opinion dated Nov. 12, 2019 for Application No. EP 19186244.0, 7 pgs.
European Search Report dated Aug. 7, 2018 for Application No. 18157228.0, 14 pages.
European Search Report, Extended, and Written Opinion dated Jan. 31, 2020 for Application No. EP 119186252.3, 14 pgs.
European Search Report, Extended, and Written Opinion dated Dec. 10, 2019 for Application No. EP 19186231.7, 7 pgs.
European Search Report, Partial, and Provisional Written Opinion dated Oct. 31, 2019 for Application No. EP 119186252.3, 16 pgs.
European Search Report, Partial, and Written Opinion dated May 4, 2018 for Application No. EP 18157228.0, 18 pages.
European Search Report, Partial, and Written Opinion dated Dec. 9, 2019 for Application No. EP 19186224.2, 11 pgs.
International Search Report and Written Opinion dated Jan. 2, 2020 for Application No. PCT/IB2019/056041, 11 pgs.
International Search Report and Written Opinion dated Feb. 27, 2020 for Application No. PCT/IB2019/055983, 20 pgs.
International Search Report and Written Opinion dated Dec. 6, 2019 for Application No. PCT/IB2019/055980, 13 pgs.
International Search Report and Written Opinion dated Apr. 19, 2018 for International Application No. PCT/ JS2018/017751, 17 pages.
Japanese Office Action, Notification of Reasons for Refusal, and Search Report by Registered Search Organization, dated Nov. 9, 2021 for Application No. JP 2019-544695, 26 pgs.
Design U.S. Appl. No. 29/594,332, filed Feb. 17, 2017.
Design U.S. Appl. No. 29/594,335, filed Feb. 17, 2017.
Design U.S. Appl. No. 29/594,340, filed Feb. 17, 2017.
U.S. Appl. No. 11/851,495, filed Sep. 7, 2007.
U.S. Appl. No. 14/868,718, filed Sep. 29, 2015.
U.S. Appl. No. 15/435,573, filed Feb. 17, 2017.
U.S. Appl. No. 15/435,607, filed Feb. 17, 2017.
U.S. Appl. No. 15/435,618, filed Feb. 17, 2017.
U.S. Appl. No. 15/435,631, filed Feb. 17, 2017.
U.S. Appl. No. 16/035,803, filed Jul. 16, 2018.
U.S. Appl. No. 16/035,821, filed Jul. 16, 2018.
U.S. Appl. No. 16/035,825, filed Jul. 16, 2018.
U.S. Appl. No. 16/035,831, filed Jul. 16, 2018.
U.S. Appl. No. 16/035,834, filed Jul. 16, 2018.
U.S. Appl. No. 16/035,856, filed Jul. 16, 2018.
U.S. Appl. No. 16/035,860, filed Jul. 16, 2018.
U.S. Appl. No. 16/035,872, filed Jul. 16, 2018.
U.S. Appl. No. 16/035,893, filed Jul. 16, 2018.
U.S. Appl. No. 60/466,378, filed Apr. 29, 2003.
U.S. Appl. No. 60/843,254, filed Sep. 8, 2006.
Chinese Search Report from Chinese Patent Application No. 2018800254324, dated Feb. 21, 2023, 3 pages.
Chinese Search Report from Chinese Patent Application No. 2019800591375, dated Sep. 22, 2023, 2 pages.
Notification of Reasons for Refusal from Japanese Patent Application No. 2021-502529, dated Mar. 10, 2023, 7 pages.
Notification of the First Office Action from Chinese Patent Application No. 2018800254324, dated Feb. 28, 2023, 8 pages.
Notification of the First Office Action from Chinese Patent Application No. 2019800591375, dated Sep. 23, 2023, 9 pages.

* cited by examiner

SURGICAL STAPLING END EFFECTOR COMPONENT WITH TIP HAVING VARYING BEND ANGLE

PRIORITY

This application is a continuation of U.S. Non-Provisional patent application Ser. No. 16/035,856, filed Jul. 16, 2018, entitled "SURGICAL STAPLING END EFFECTOR COMPONENT WITH TIP HAVING VARYING BEND ANGLE," issued as U.S. Pat. No. 11,564,684 on Jan. 31, 2023, which is a continuation-in-part of U.S. Non-Provisional patent application Ser. No. 15/435,573, filed Feb. 17, 2017, entitled "SURGICAL STAPLER WITH ELASTICALLY DEFORMABLE TIP," issued as U.S. Pat. No. 10,828,031 on Nov. 10, 2020, the disclosures of which is are incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
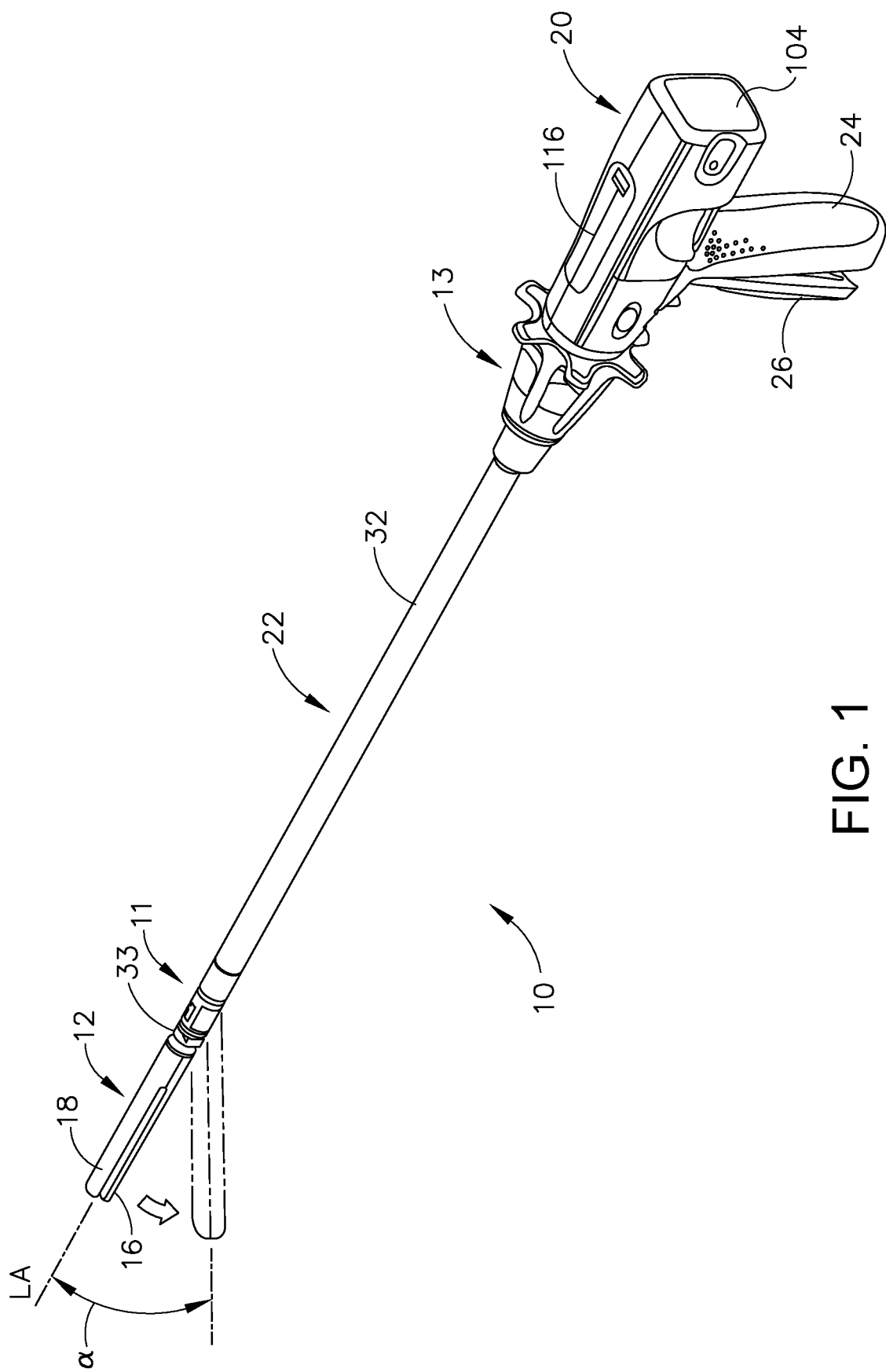
FIG. 1 depicts a perspective view of an exemplary articulating surgical stapling instrument.
Figure 2:
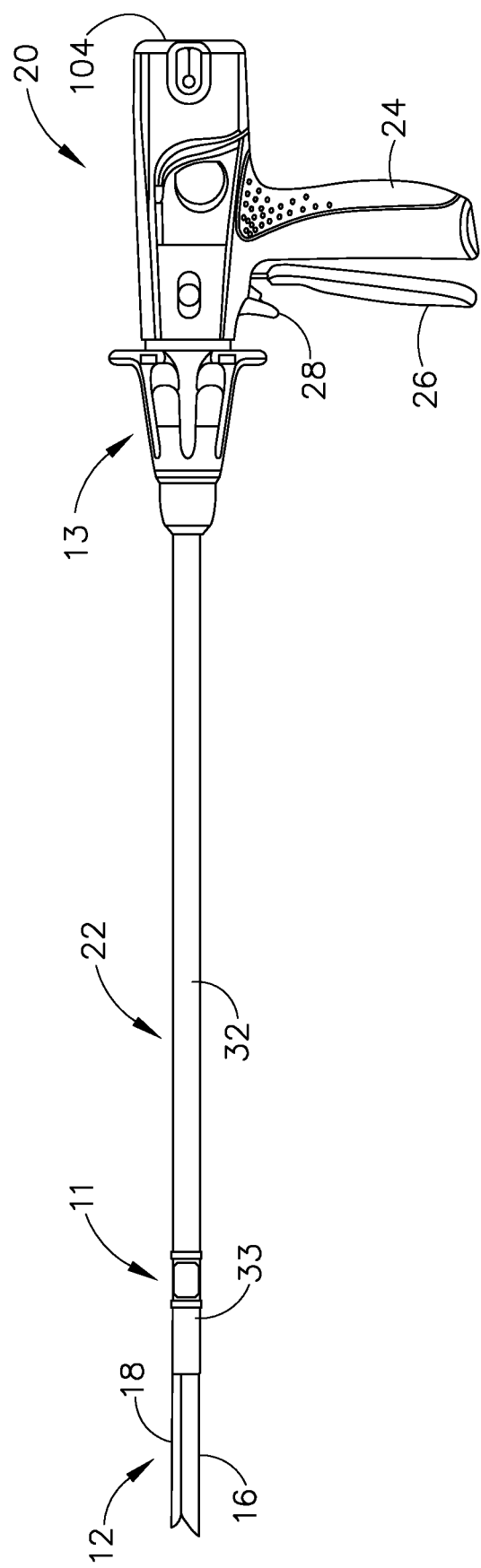
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical," "horizontal," "upper," and "lower" are used herein with respect to the drawings. However, surgical instruments are used in many orientations and positions, and these terms are not intended to be limiting and absolute.

In some versions, shaft (22) is constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle ($\alpha$). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein. Articulation joint (11) may also be constructed and operable in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In the present example, anvil (18) can also be considered an upper jaw. Furthermore, in some versions like the present example, the upper jaw or anvil (18) pivots with respect to a stationary lower jaw (16); however, in some other versions the upper jaw or anvil (18) is stationary while the lower jaw (16) pivots. In some versions, lower jaw (16) is constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; at least some of the teachings of U.S. Pat. No. 9,839,421, entitled "Jaw Closure Feature for End Effector of Surgical Instrument," issued Dec. 12, 2017, the disclosure of which is incorporated by reference herein; and/or at least some of the teachings of U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein. Other suitable forms that firing beam (14) may take will be apparent to those of ordinary skill in the art in view of the teachings herein.

Figure 3:
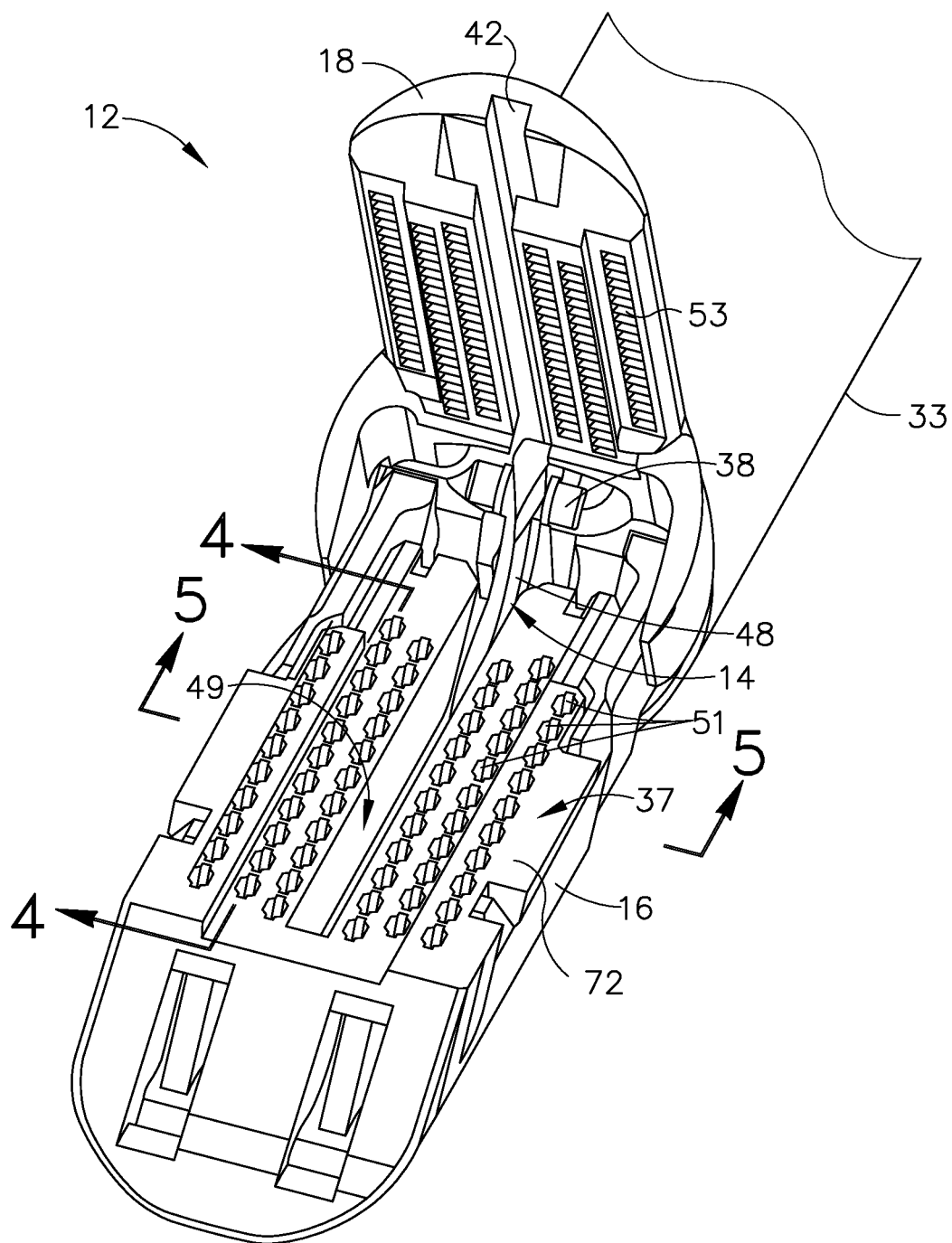
FIG. 3 depicts a perspective view of an opened end effector of the instrument of FIG. 1.
Figure 4A:
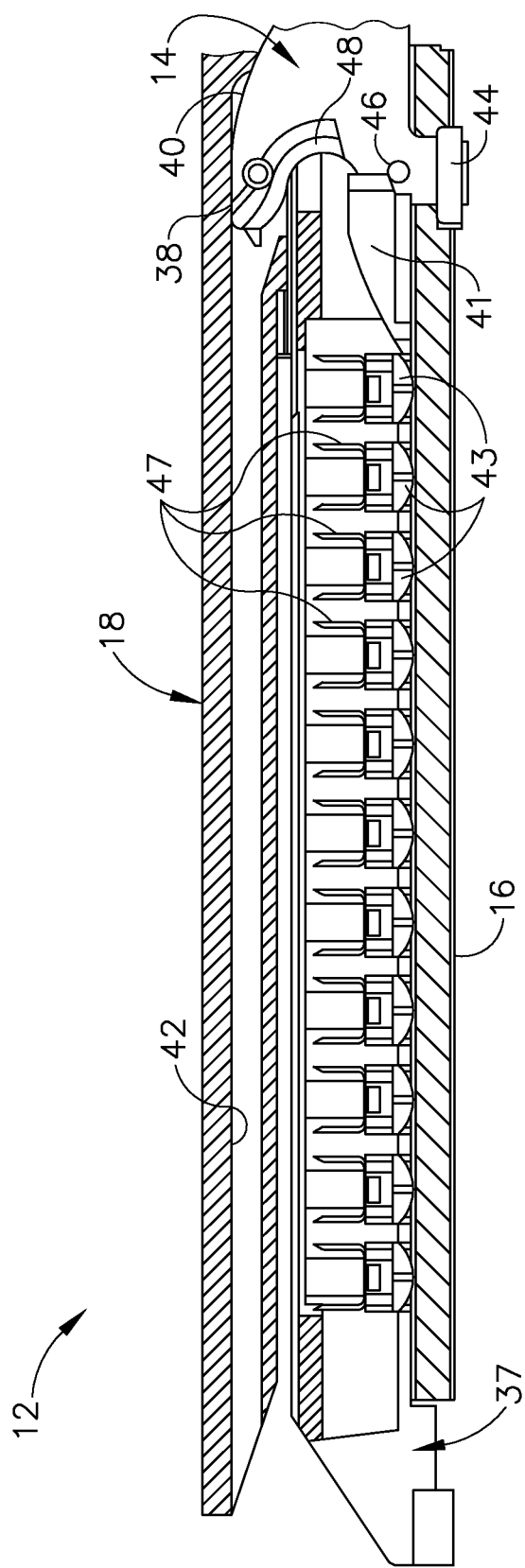
FIG. 4A depicts a side cross-sectional view of the end effector of FIG. 3, taken along line 4-4 of FIG. 3, with the firing beam in a proximal position.
Figure 4B:
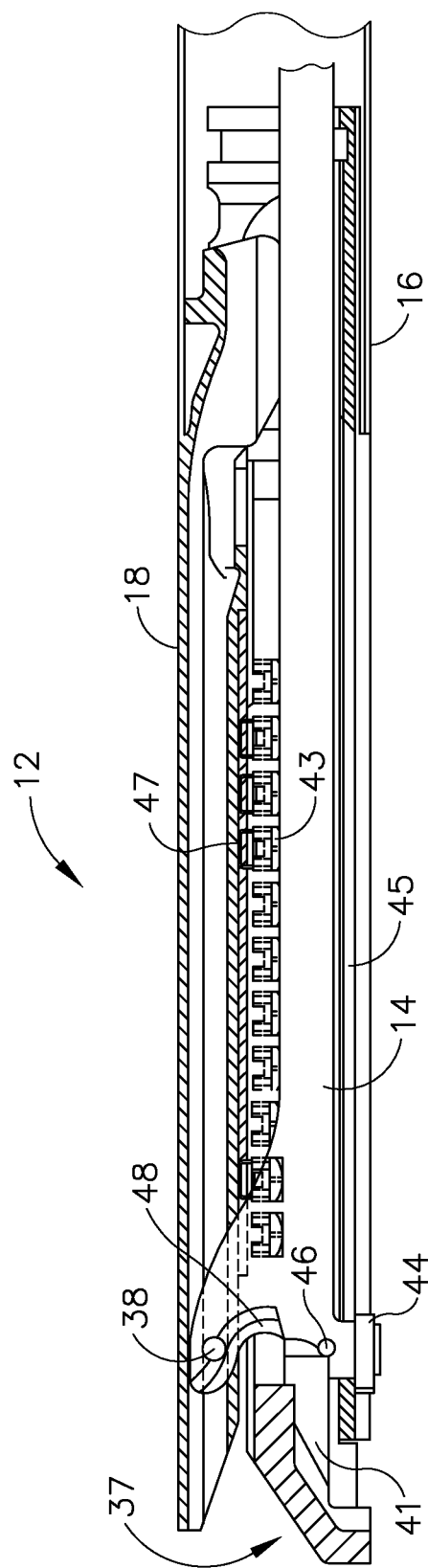
FIG. 4B depicts a side cross-sectional view of the end effector of FIG. 3, taken along line 4-4 of FIG. 3, with the firing beam in a distal position.
Figure 5:
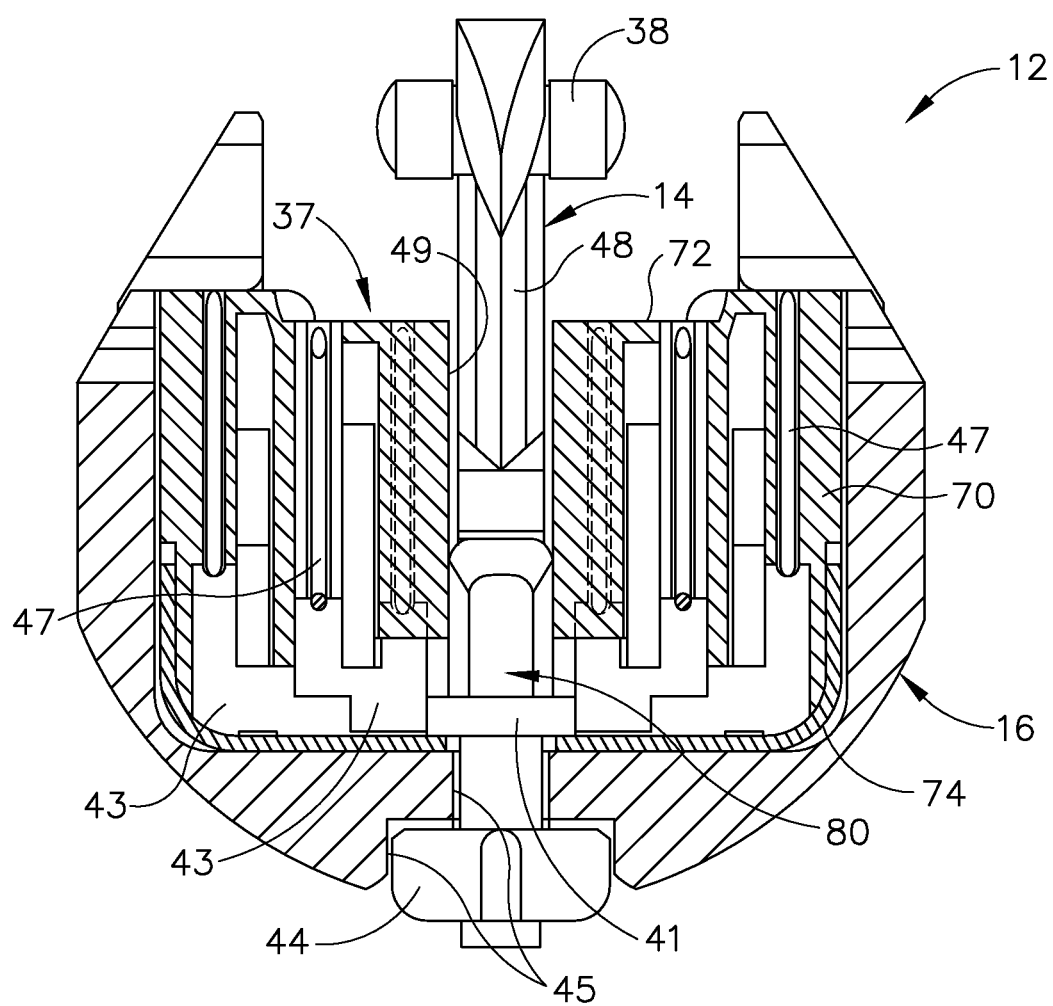
FIG. 5 depicts an end cross-sectional view of the end effector of FIG. 3, taken along line 5-5 of FIG. 3.
Figure 6:
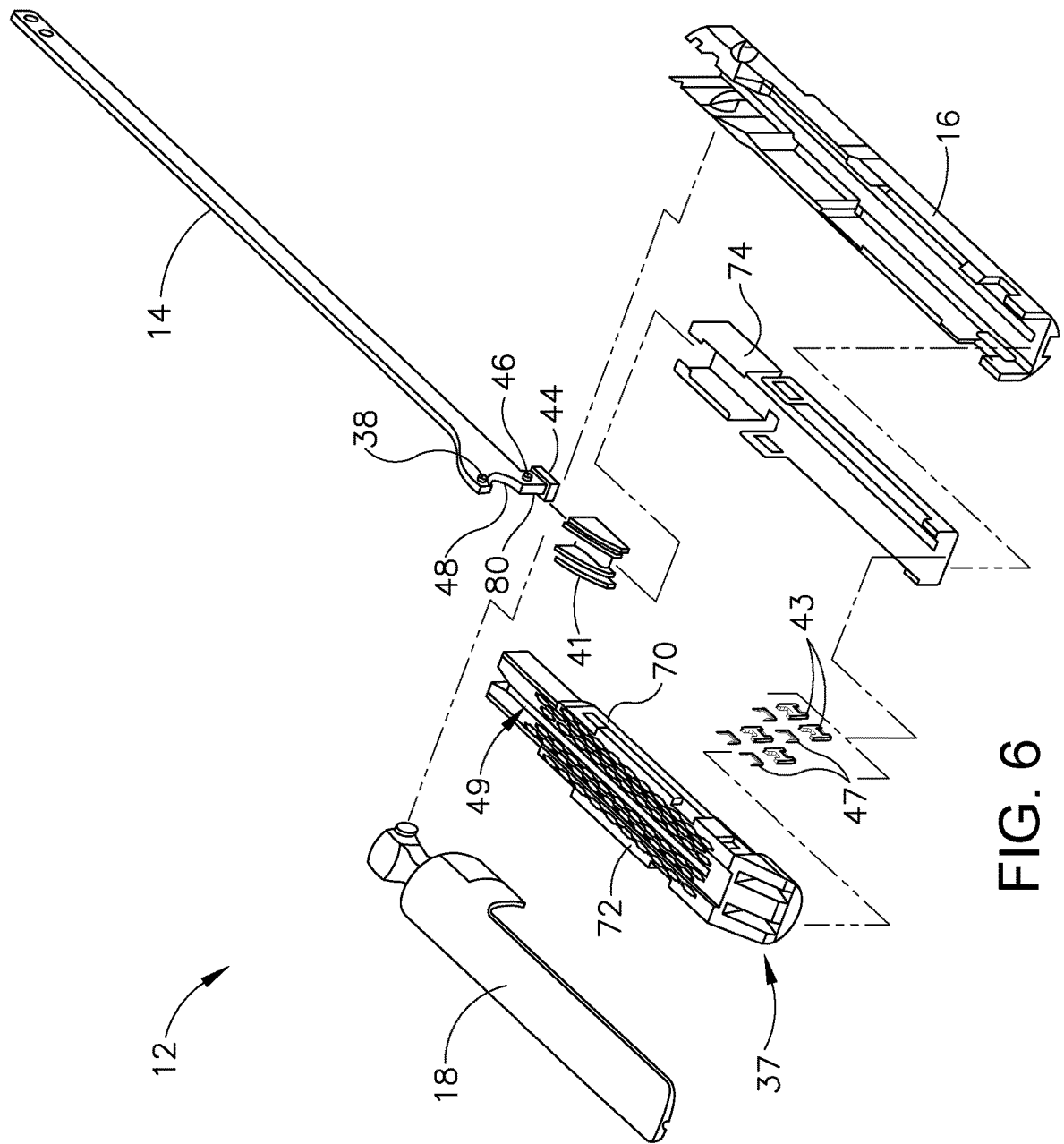
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein. In addition or in the alternative, staple cartridge (37) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
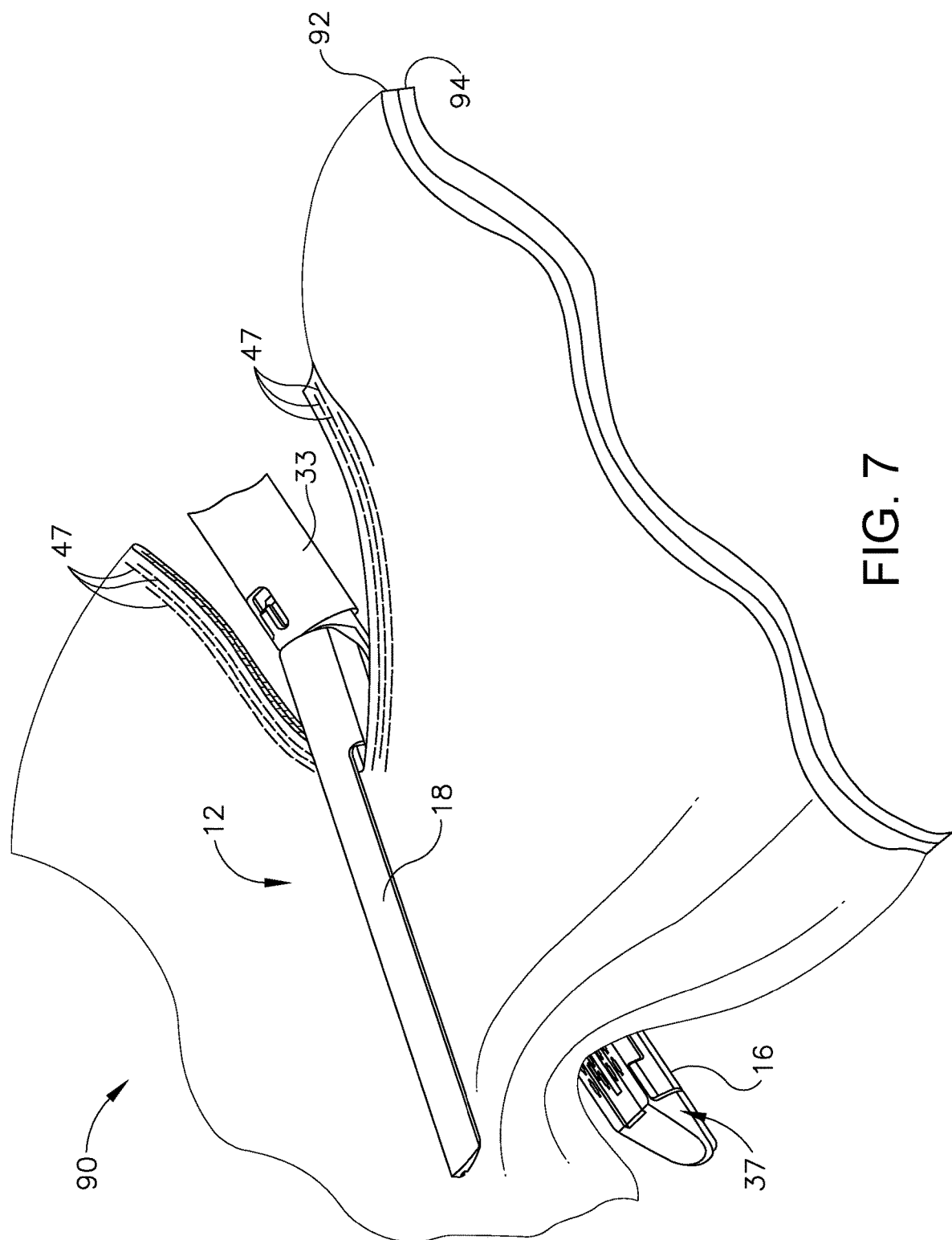
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in U.S. Pat. No. 9,622,746, entitled "Distal Tip Features for End Effector of Surgical Instrument," issued Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pat. No. 8,453,914, the disclosure of which is incorporated by reference herein; and/or in accordance with at least some of the teachings of U.S. Pat. No. 8,453,914, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in U.S. Pat. No. 9,622,746, entitled "Distal Tip Features for End Effector of Surgical Instrument," issued Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; 8,408,439; and/or 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effector with Visualization, Lead-In, and Gathering Feature In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
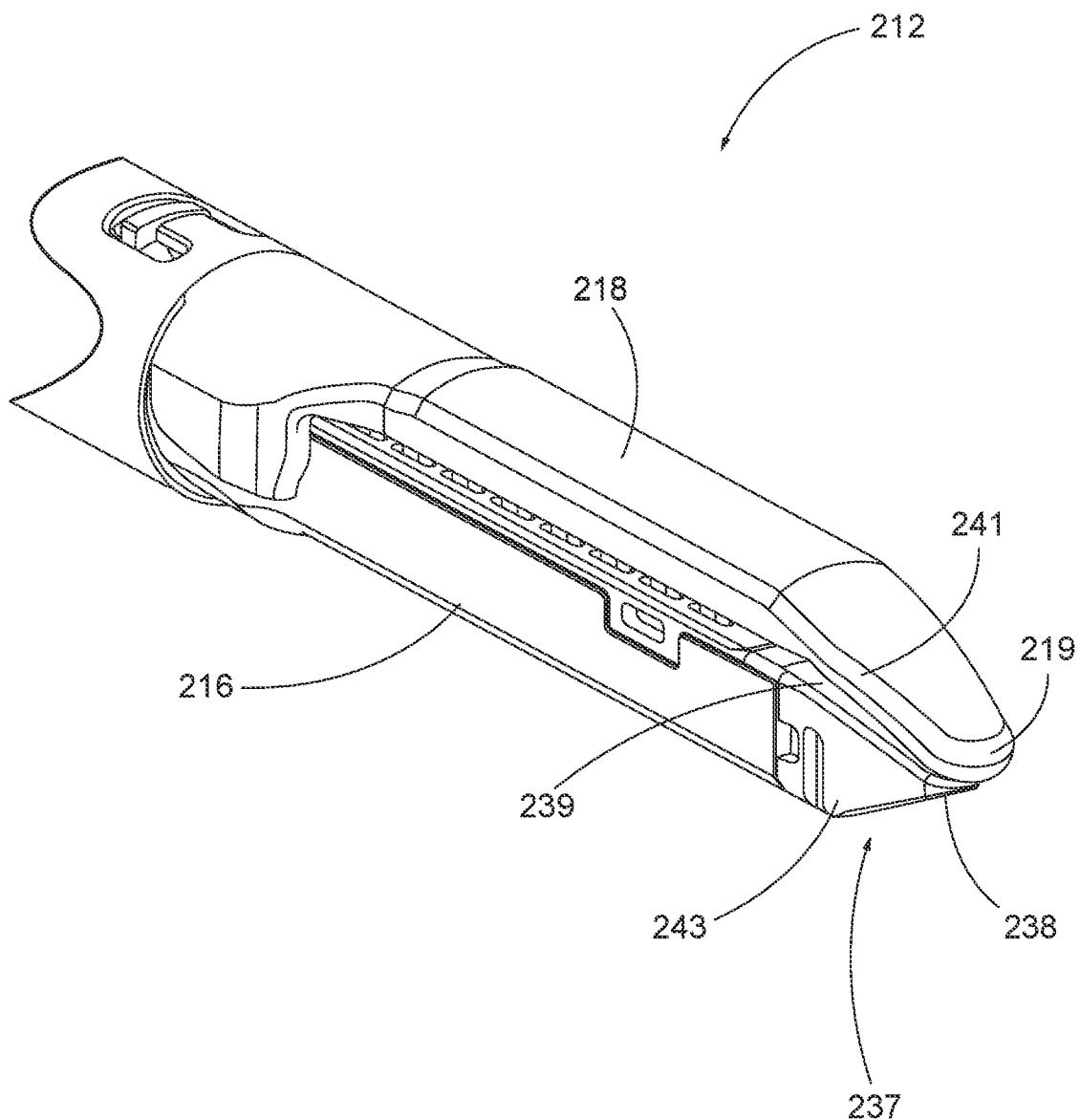
FIG. 8 depicts a perspective view of an alternative version of an end effector with an angled anvil and an angled cartridge.

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
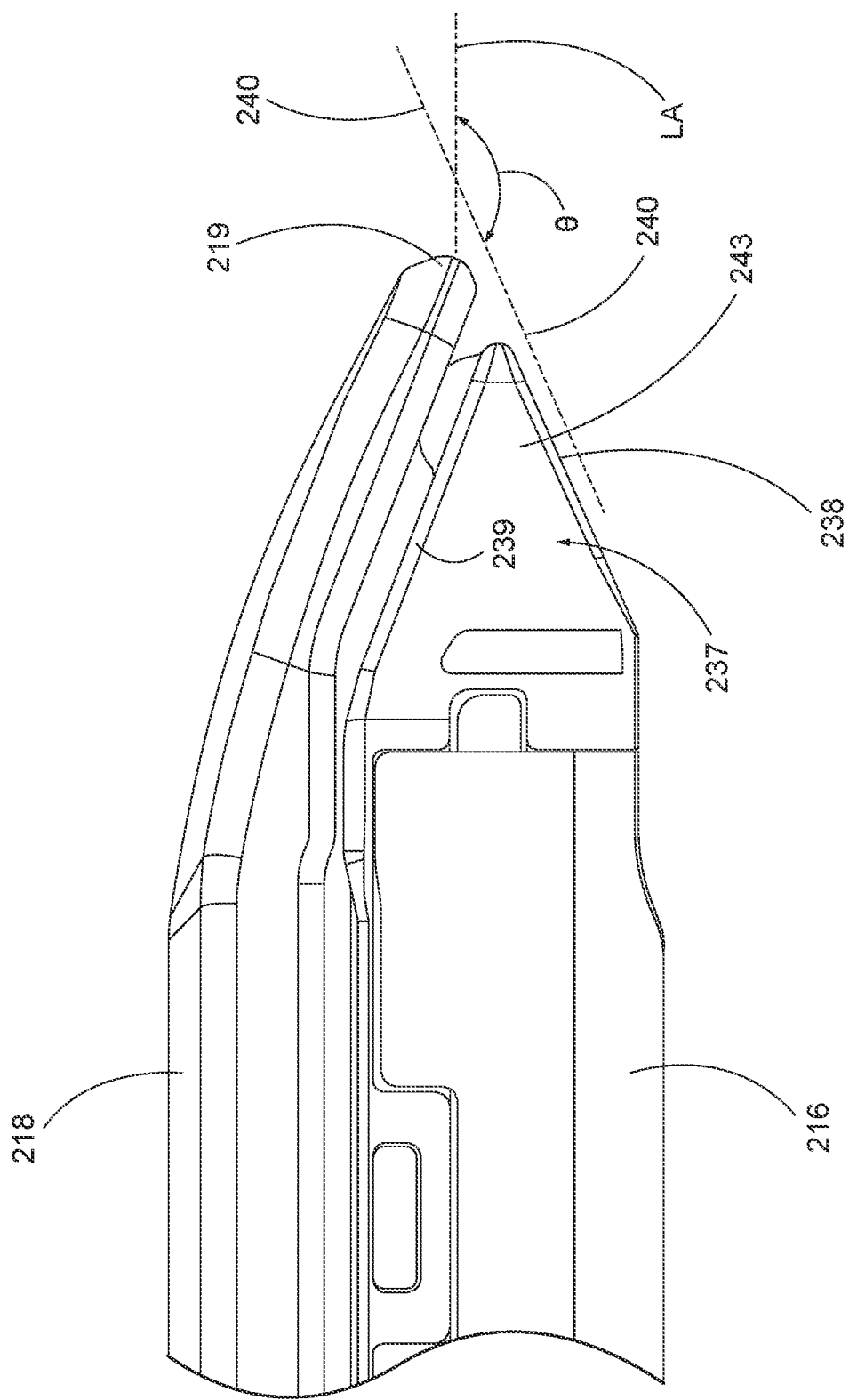
FIG. 9 depicts an enlarged, side view of the end effector of FIG. 8.
Figure 10:
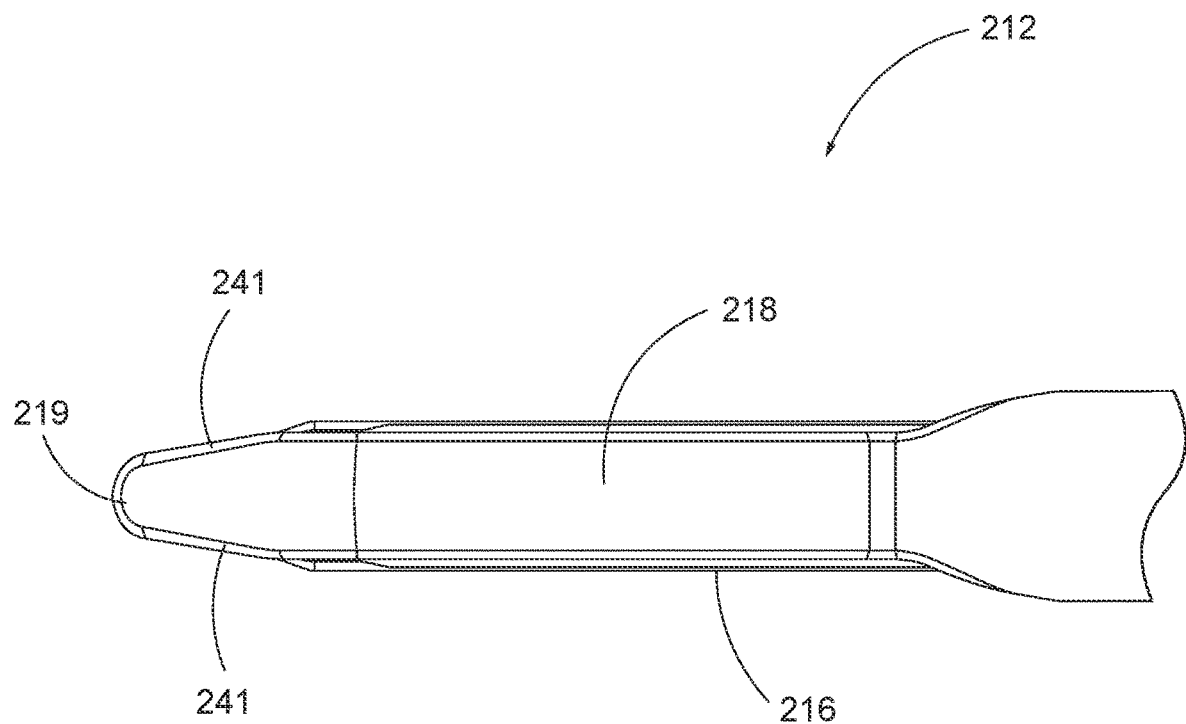
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle (θ).

Viewing angle (θ) may establish the relative visibility that a user has regarding distal tip (219). In particular, the user can see in front of distal tip (219) along any line of sight that passes through the intersection of sight line (240) and longitudinal axis (LA) within viewing angle (θ). For instance, as viewing angle (θ) increases, the user would have greater visibility of the area immediately in front of distal tip (219) from proximal vantage points; whereas as viewing angle (θ) decreases, the user has less visibility of the area in front of distal tip (219) from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (212) will be described in greater detail below.

III. Exemplary End Effectors with Bent or Angled Elastically Deformable Anvil Tips In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). However, in versions where all the structures of end effector (212) are rigid, the bent configuration of distal tip (219) of anvil (218) may not lend itself well to marching operations, as distal tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

Figure 11:
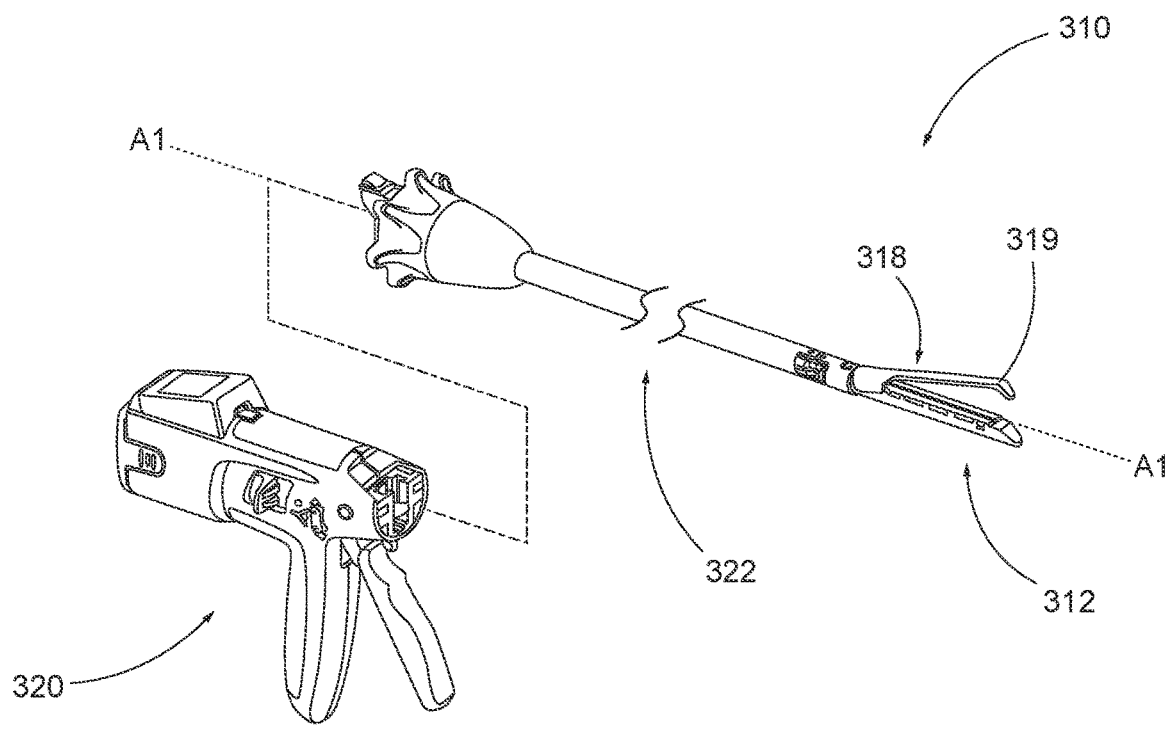
FIG. 11 depicts a perspective view of an exemplary surgical stapling instrument having an end effector with a bent or angled elastically deformable tip section.

FIG. 11 shows another exemplary instrument (310) configured as a surgical stapler. Instrument (310) comprises a handle portion (320) and a shaft (322). Instrument (310) has a modular configuration such that shaft (322) is selectively removable from, and attachable to, handle portion (320).

Instrument (310) is configured similarly to instrument (10) such that the operability and use of instrument (310) is the same as described above for instrument (10) with the added feature of instrument (310) being a modular configuration. With its modular configuration, instrument (310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (310) may be configured in accordance with at least some of the teachings of U.S. Pub. No. 2017/086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein. Other suitable components, features, and configurations for providing instrument (310) with a modular configuration will be apparent to those of ordinary skill in the art in view of the teachings herein. Moreover, it will be understood by those of ordinary skill in the art in view of the teachings herein, that instrument (10) may be modified to incorporate a modular configuration as shown and described with respect to instrument (310) or other instruments incorporated by reference herein.

In the illustrated example of FIG. 11, instrument (310) comprises an end effector (312) having an anvil (318) that has an angled distal tip (319). Furthermore, distal tip (319) of anvil (318) is elastically deformable. In this manner, and as shown best in FIGS. 12A and 12B, angled distal tip (319) is operable to elastically deform from a first angled position to a second position. The second position for angled distal tip (319) may be substantially straight in some versions, but may be angled to a degree (e.g., slightly above or slightly below the longitudinal axis (A1)) in other versions. It should be understood that the second position for angled distal tip (319) may be defined by the characteristics (e.g., thickness, density, etc.) of the tissue that is being captured between anvil (318) and lower jaw (16). In the present example, end effector (312) is provided on shaft (322) that is detachable from handle portion (320). By way of example only, shaft (322) may be detachable from handle portion (320) in accordance with at least some of the teachings of U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

It will be appreciated that end effector (312) may be used in place of end effector (12) shown in FIG. 1. In some versions, end effector (312) may be integrally formed with shaft (22) or alternatively may be separately formed and then combined. In some versions, end effector (312) may be provided for use in robotic systems. In such robotic systems, modular shaft (322) having end effector (312) may be attachable to a portion of the robotic system for use such that handle portion (320) is replaced by components of the robotic system. Still in other examples, end effector (312) may be adapted for use with a robotic system in a manner where end effector (312) connects with the robotic system without necessarily connecting the entire modular shaft (322). In view of the teachings herein, other ways to incorporate an end effector having an angled elastically deformable anvil tip into a user operated or robotic operated instrument will be apparent to those of ordinary skill in the art.

Figure 12A:
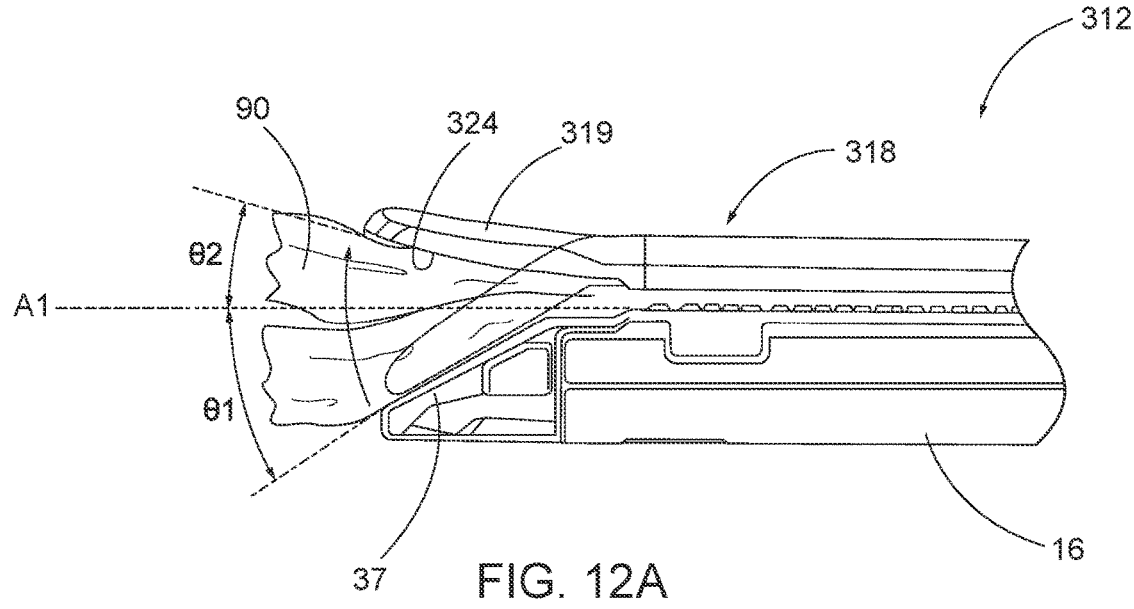
FIG. 12A depicts an enlarged side view of a distal portion of the end effector of FIG. 11.

FIG. 12A shows an enlarged side view of the distal end of end effector (312). End effector (312) comprises anvil (318) and lower jaw (16) that accepts cartridge (37) as described above with respect to instrument (10). Anvil (318) pivotably rotates toward lower jaw (16) in the same manner as anvil (18) as described above with respect to instrument (10). In this configuration, end effector (312) is similar to end effector (12), however, anvil (318) comprises angled distal tip (319) that is elastically deformable. As shown in FIG. 12A, tip (319) is imparted with a bias to an angled position that is shown in FIG. 11 and in phantom in FIG. 12A. Tip (319) assumes this angled position when end effector (312) is not clamping tissue and is open, as shown in FIG. 11; or closed without clamping tissue, as shown in phantom in FIG. 12A. In instances when end effector (312) is in this angled state or position, end effector (312) can be considered not loaded or in a non-loaded state or position. Conversely when end effector (312) is clamping tissue, end effector (312) can be considered loaded or in a loaded state or position.

When closed and not clamping tissue between anvil (318) and lower jaw (16), tip (319) contacts cartridge (37). In this position, an underside surface (324) of tip (319) defines a plane that intersects a longitudinal axis (A1) defined by shaft (322) to form an angle (θ1). When closed and clamping tissue (90) between anvil (318) and lower jaw (16), underside surface (324) of tip (319) contacts tissue (90). In this position, underside surface (324) of tip (319) defines a plane that intersects longitudinal axis (A1) to form an angle (θ2). In the illustrated example of FIG. 12A, angles (θ1, θ2) are relative to longitudinal axis (A1), and the sum of angles (θ1, θ2) represent the range of motion distal tip (319) undergoes. By way of example only, and not limitation, in some examples angle (θ1) is between about 20 and about 70 degrees, or more particularly between about 30 degrees and about 50 degrees, in a downward direction from longitudinal axis (A1) toward cartridge (37). By way of example only, and not limitation, in some examples angle (θ2) is between about 0 and about 90 degrees in an upward direction from longitudinal axis (A1) away from cartridge (37). By way of example only, and not limitation, in some examples the range of motion undergone by tip (319) is between about 20 degrees and about 110 degrees. The angles described for angles (θ1, θ2) are exemplary only and not limiting. Other suitable angles will be apparent to those of ordinary skill in the art in view of the teachings herein.

Additionally, in some instances longitudinal axis (A1) represents a zero-degree reference and angles relative thereto may be positive or negative. For instance, where an angle is in a downward direction from longitudinal axis (A1) toward cartridge (37), the angle may be characterized as a negative angle. Similarly, where an angle is in an upward direction from longitudinal axis (A1) away from cartridge (37), the angle may be characterized as a positive angle. When using these conventions, the range of motion of distal tip (319) due to deformation can be understood as the sum of the absolute value of the angle when distal tip (319) is in the position contacting cartridge (37), and the angle when distal tip (319) is in the deformed state when clamping tissue.

Figure 12B:
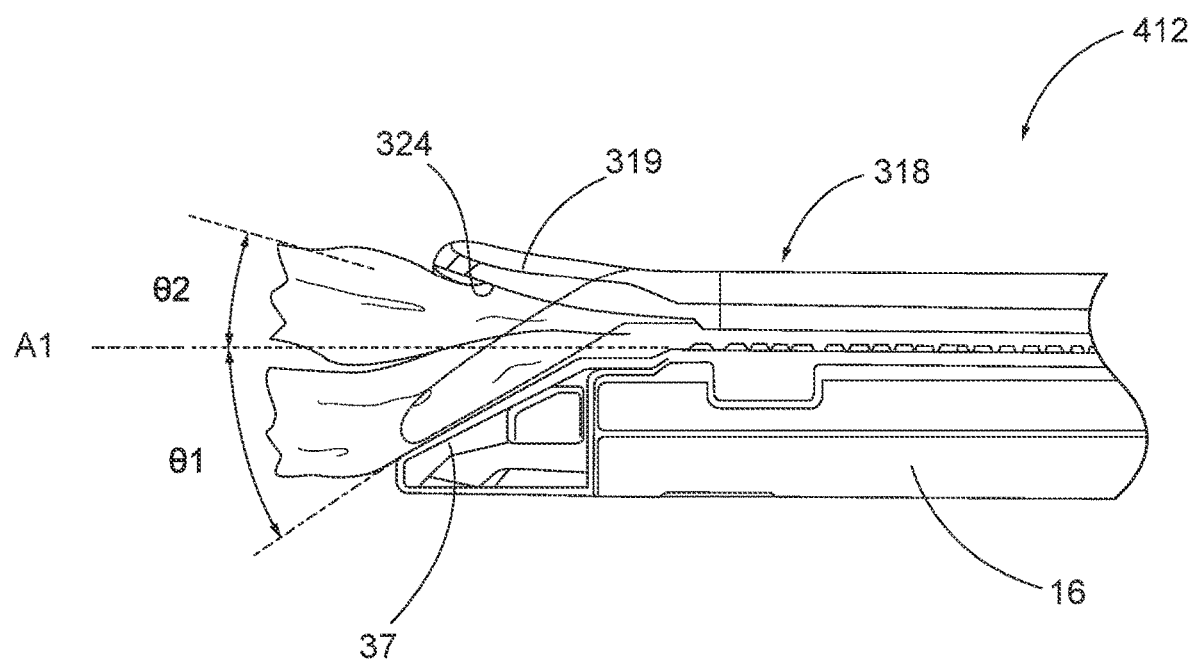
FIG. 12B depicts an enlarged side view of a distal portion of an alternate end effector similar to that of FIG. 11.

FIG. 12B shows another side view of an alternate end effector (412) similar to end effector (312) of FIG. 12A. With end effector (312), when anvil (318) is in its angled and non-deformed state (as seen in phantom in the view of FIG. 12A), anvil (318) extends to a point even with or proximal to the distal most end of cartridge (37). When anvil (318) is deformed such that it is deflected upwardly, the end of distal tip (319) extends to a point just distal to the distal most end of cartridge (37). With end effector (412), as shown in FIG. 12B, when anvil (318) is in its angled and non-deformed state (as seen in phantom in the view of FIG. 12B), anvil (318) extends to a point even with or proximal to the distal most end of cartridge (37). When anvil (318) is deformed such that it is deflected upwardly, the end of a distal tip (319) of anvil (318) extends to a point even with or proximal to the distal most end of cartridge (37). In this manner, anvil (318) of end effector (412) remains even with or proximal to the distal most end of cartridge (37) when anvil (318) is in its angled state or deformed state such that anvil (318) does not extend past the distal most end of cartridge (37) whether anvil (318) is in its angled and non-deformed state or in its deformed state. In some instances, this can be achieved by modifying anvil (318) such that distal tip (319) of anvil is shortened in length. In other instances, instruments (10, 310) may be modified to provide for a slight proximal retraction of anvil (318) when clamping. In view of the teachings herein, other ways to modify end effector (412) as it relates to control of anvil (318) position, will be apparent to those of ordinary skill in the art.

A. Overmolded Anvil Tip

Figure 13:
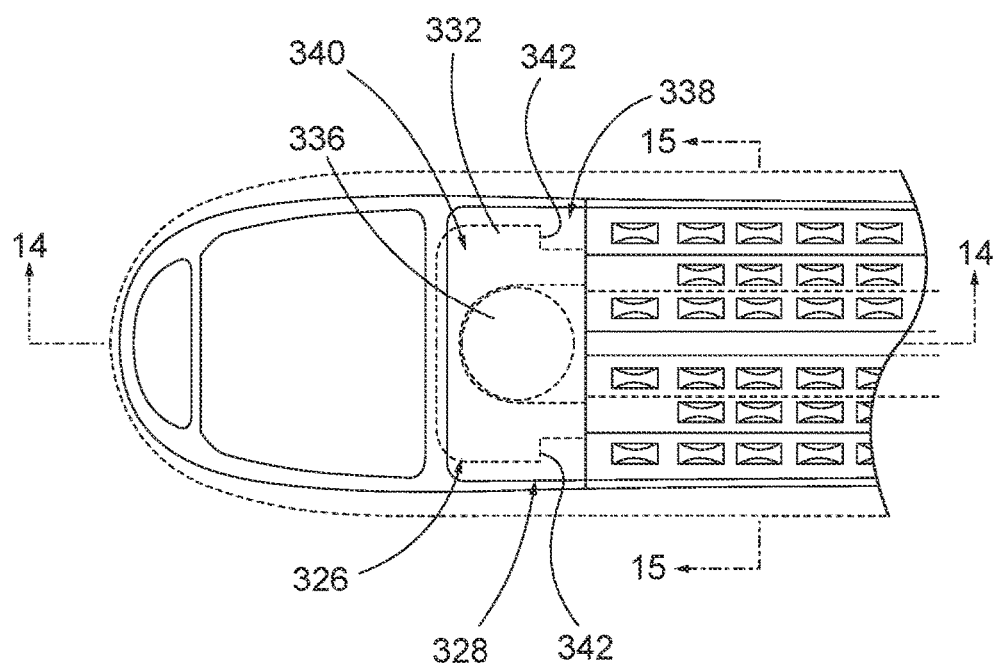
FIG. 13 depicts a bottom view of a distal portion of the end effector of FIG. 11 with the cartridge shown in phantom to reveal an underside surface of the anvil.
Figure 14:
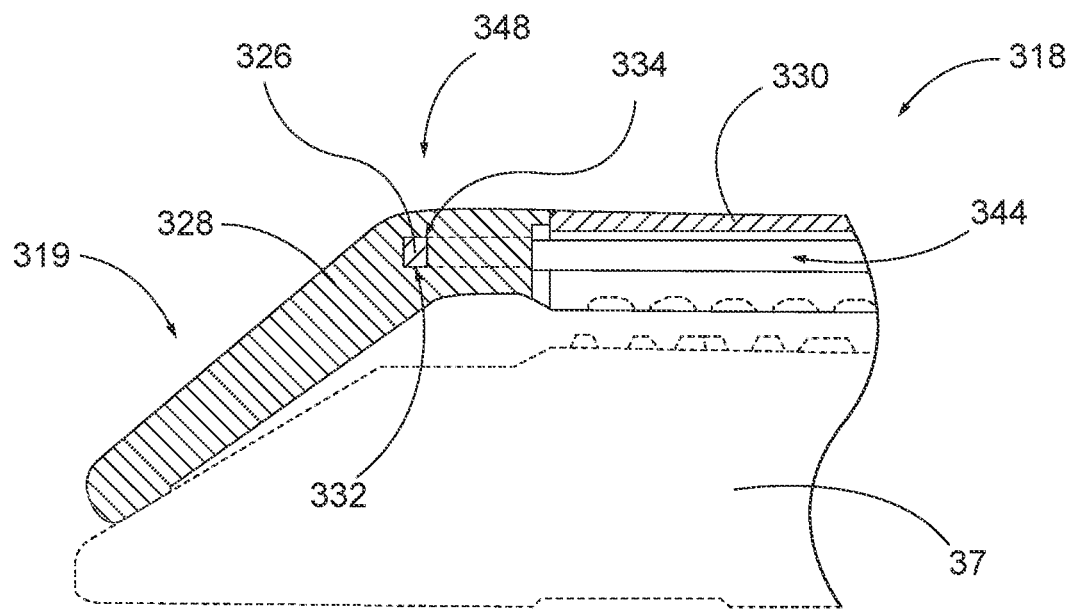
FIG. 14 depicts a side cross-sectional view of a distal portion of the end effector of FIG. 11, taken along line 14-14 of FIG. 13.
Figure 15:
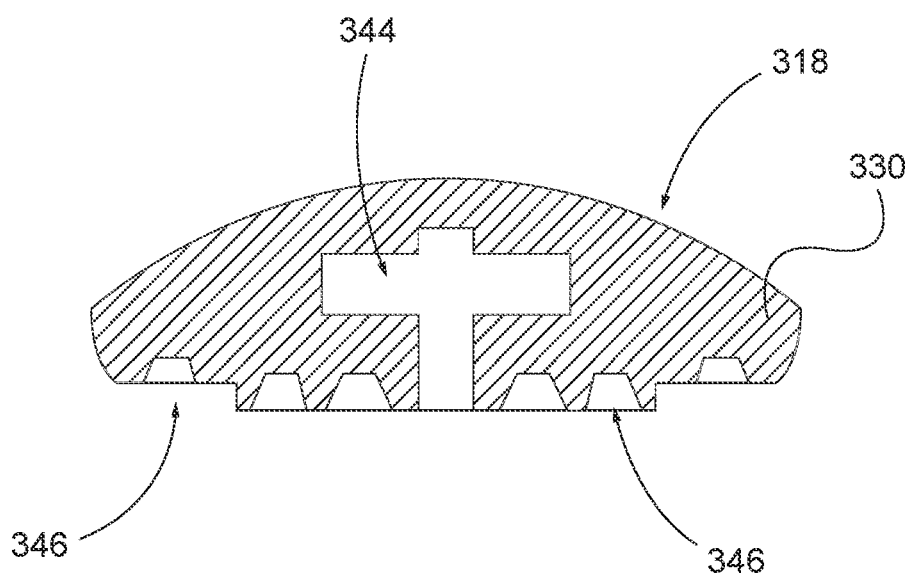
FIG. 15 depicts an end cross-sectional view of an anvil the end effector of FIG. 11, taken along line 15-15 of FIG. 13.

FIGS. 13-15 show enlarged distal views of end effector (312) to illustrate an exemplary construction. The constructions shown in FIGS. 13-15 also applies to end effector (412) shown in FIG. 12B, except for the anvil (318) length difference noted above. As shown in the top view of FIG. 13, end effector (312) comprises anvil (318) where distal tip (319) comprises a rigid portion (326) and a deflectable portion (328). In the present example, deflectable portion (328) is overmolded onto rigid portion (326) to form distal tip (319) of anvil (318). In the illustrated example as shown in FIG. 13, the outline of cartridge (37) is shown in phantom to reveal underside surface (324) of anvil (318). Rigid portion (326) of distal tip (319) extends from a body (330) of anvil (318). In the present example, body (330) is comprised of metal and rigid portion (326) is an extension of metal body (330) into distal tip (319). In other versions, body (330) and/or rigid portion (326) can be comprised of materials other than metal, including but not limited to plastic, ceramic, combinations of metal with plastic or ceramic, and other suitable materials or combinations of materials that will be apparent to those of ordinary skill in the art in view of the teachings herein. Additionally, rigid portion (326) in some versions is entirely rigid, yet in other versions rigid portion (326) can be resilient to a lesser extent than deflectable portion (328).

In the illustrated version of FIGS. 13 and 14, metal portion (326) comprises an underside surface (332) that is generally flat or planar, and a top surface (334) that is similarly generally flat or planar. Metal portion (326) further comprises an opening (336) that extends through metal portion (326) from top surface (334) to underside surface (332). Additionally, metal portion (326) comprises a neck region (338), a head region (340) that extends distally from neck region (338), and shoulders (342) at the transition between neck region (338) and head region (340). In the present example neck region (338) extends from body (330) of anvil (318). With this arrangement, metal portion (326) provides securing features or interfaces, such as opening (336) and shoulders (342), where elastomeric portion (328) can connect with metal portion (326) in a secure fashion using an overmolding process.

FIG. 15 illustrates a cross section view of anvil (318) just proximal to distal tip (319). As shown, anvil (318) comprises a longitudinal slot (344) that divides six rows of staple forming pockets (346) into two sets of three rows each. Slot (344) and staple forming pockets (346) are structurally and functionally similar to slot (42) and staple forming pockets (53) described above with respect to anvil (18). Slot (344) comprises a "t" shaped cross section as shown in FIG. 15. Referring again to FIGS. 13 and 14, opening (336) in metal portion (326) is positioned adjacent to a laterally extending portion of slot (344). In view of the teachings herein, other ways to configure metal portion (326) for suitable connection with elastomeric portion (328) using an overmolding process will be apparent to those of ordinary skill in the art.

Elastomeric portion (328) is molded onto metal portion (326) and in the molding process is imparted with an angled configuration such that elastomeric portion (328) defines a plane that intersects and is not co-planar with a plane defined by body (330) of anvil (318). In this manner, elastomeric portion (328) is formed with a bias to maintain its angled configuration unless some other force is imparted onto elastomeric portion (328) causing it to deflect from its initial angled position. During the molding process, elastomeric material flows through and fills opening (336) in metal portion (326). Elastomeric material also flows around and adjacent to shoulders (342). In this manner, elastomer portion (328) is securely connected with metal portion (326) during the overmolding process. Elastomeric portion (328) may comprise rubber, plastic, or any other suitable natural or synthetic material having the desired elastomeric properties that will allow distal tip (319) to deform when subject to force, yet resiliently return to its initial angled state when the force is no longer applied or present. During the molding process, a stop member (not shown) may be inserted into a slot (349) formed distally to slot (344), to prevent the elastomeric material from entering slot (344). In view of the teachings herein, other ways to configure elastomeric portion (328) for suitable connection with metal portion (326) using an overmolding process will be apparent to those of ordinary skill in the art.

With the configuration for distal tip (319) as described above and shown in FIGS. 13 and 14, the extension of metal portion (326) into the region of distal tip (319) defines a deflection zone (348). Deflection zone (348) coincides with a rigid portion of distal tip (319) located at a proximal end of distal tip (319). With this area of increased rigidity, distal tip (319) will deflect, for example as shown in FIG. 12A, with deflection zone (348) serving as a pivot point or location about which the remainder of distal tip (319) rotates during deflection. In view of the teachings herein, those of ordinary skill in the art will appreciate other ways in which to modify distal tip (319) to alter, modify, or control deflection zone (348) such that a desired deflection of distal tip (319) is achieved.

IV. Exemplary Configurations for End Effectors with Elastically Deformable Placement Tips With end effectors having bent or angled elastic deformable tips, also referred to as placement tips, such as those described above with respect to end effectors (312, 412), the deformable tips can deflect during use. As described above, the elastic deformable tip can be located on the anvil, like with anvil (318). In other versions, the elastic deformable tip can be located on the cartridge. Additionally, while end effectors (12, 212, 312, 412) described above are discussed as including a lower jaw (16, 216) opposite to the anvil (18, 218, 318), in some versions the end effectors comprise an upper jaw and a lower jaw, where the anvil may be located on either jaw, and the cartridge may be located on either jaw opposite the jaw with the anvil. Furthermore, either jaw may include the elastic deformable tip, which can be part of, or associated with, the anvil or the cartridge. The following paragraphs describe several exemplary end effectors, usable with instruments (10, 310) and other instruments, that include a lower jaw, an upper jaw, and an elastic deformable tip or placement tip. These exemplary end effectors are shown and described in a variety of ways that are not intended to be mutually exclusive of each other. Instead, in many instances the features of one version applies equally to another version, as will be appreciated by those of ordinary skill in the art in view of the teachings herein.

In some versions that will be shown and described, the deflection of the deformable tip changes an angle of the deformable tip relative to a longitudinal axis defined by the jaw with which the deformable tip is located when comparing states when the end effector is in open versus closed states. In some versions that will be shown and described, the deflection of the deformable tip changes an angle of the deformable tip relative to the nose of the cartridge when the end effector is loaded or engages tissue versus when the end effector is not loaded or not engaged with tissue. In some versions that will be shown and described, the placement tip of one of the end effector jaws may adopt certain positions relative to the other of the end effector jaws when in deflected versus non-deflected states. In some versions that will be shown and described, the end effector components are configured with certain placement tip end and/or width profiles. Lastly, in some versions that will be shown and described, the end effector components are configured with certain underside surface configurations and/or gaps.

The end effectors described below can each be configured for use with instruments (10, 310) described above. For instance, it will be appreciated that each of the end effectors described below may be used in place of end effector (12) shown in FIG. 1 or in place of end effector (312) shown in FIG. 11. In some versions, each of the end effectors described below may be integrally formed with shaft (22) or alternatively may be separately formed and then combined. In some versions, each of the end effectors described below may be provided for use in robotic systems. In such robotic systems, modular shaft (322) having any of the end effectors described below may be attachable to a portion of the robotic system for use such that handle portion (320) is replaced by components of the robotic system. Still in other examples, each of the end effectors described below may be adapted for use with a robotic system in a manner where any of the end effectors described below connects with the robotic system without necessarily connecting the entire modular shaft (322). In view of the teachings herein, other ways to incorporate each of the end effectors described below into a user operated or robotic operated instrument will be apparent to those of ordinary skill in the art.

A. Exemplary Angles in Open and Closed States

Figure 16:
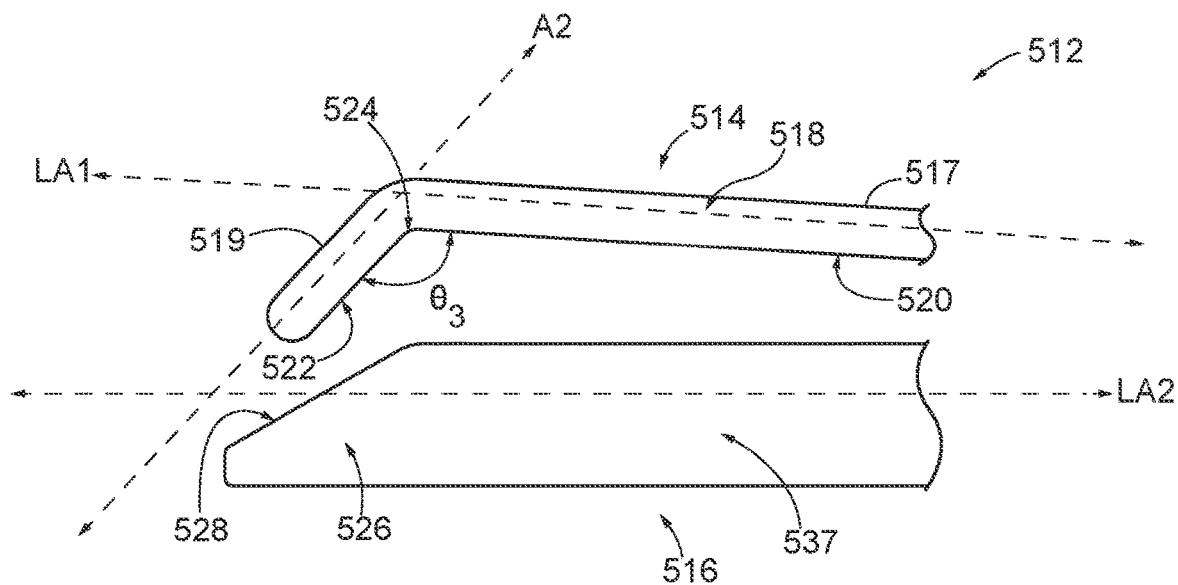
FIG. 16 depicts an enlarged side view of a distal portion of an alternative version of an end effector, shown in an open position and having an upper jaw with a placement tip that forms a first angle with a longitudinal axis of the upper jaw.
Figure 17:
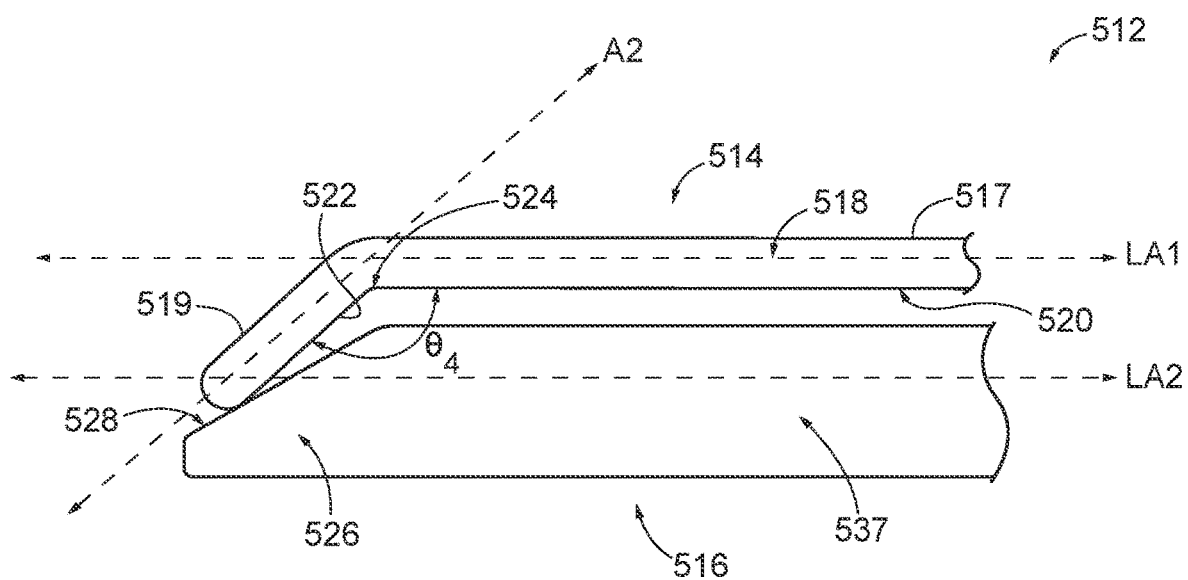
FIG. 17 depicts an enlarged side view of the distal portion of the end effector of FIG. 16, shown in a closed position and having the placement tip forming a second angle with the longitudinal axis of the upper jaw.

Referring now to FIGS. 16 and 17, an enlarged view of an end effector (512) is shown. End effector (512) is configured for use with instruments (10, 310) and/or for robotic use as described above. End effector (512) comprises an upper jaw (514) and a lower jaw (516). In the present example, upper jaw (514) comprises a body (517) having distal tip or placement tip (519) that is bent or angled and elastically deformable. Body (517), excluding placement tip (519), defines a longitudinal axis (LA1). Placement tip (519) defines another axis (A2). In the present example, longitudinal axis (LA1) extends parallel to an underside surface (520) of body (517) of upper jaw (514). Similarly, axis (A2) extends parallel to an underside surface (522) of placement tip (519).

As shown in FIG. 16, end effector (512) is in an open position or state with no tissue or other object contacting end effector (512). A first angle ($\theta 3$) is defined by the intersection of longitudinal axis (LA1) of body (517) and axis (A2) of placement tip (519). Stated another way, first angle ($\theta 3$) is defined by the intersection of a plane extending along underside surface (520) of body (517) and a plane extending along underside surface (522) of placement tip (519).

As shown in FIG. 17, end effector (512) has been moved to a closed position and still in an unloaded state without tissue contacting end effector (512). However, in the closed position, placement tip (519) of upper jaw (514) contacts lower jaw (516). With this contact and the elastically deformable nature of placement tip (519), placement tip (519) deflects from its position relative to body (517) as shown in FIG. 16. In this deflected position or state, a second angle ($\theta 4$) is defined by the intersection of longitudinal axis (LA1) of body (517) and axis (A2) of placement tip (519). Stated another way, second angle ($\theta 4$) is defined by the intersection of a plane extending along underside surface (520) of body (517) and a plane extending along underside surface (522) of placement tip (519).

With the deflection of placement tip (519), second angle ($\theta 4$) is not the same as first angle ($\theta 3$). For instance, with the illustrated deflection in FIG. 17, the lower jaw (516) contacts the underside of placement tip (519) such that placement tip (519) pivots upward away from lower jaw (516) such that the second angle ($\theta 4$) is greater than the first angle ($\theta 3$). In the present example, end effector (512) defines a pivot point (524) about which placement tip (519) pivots relative to body (517). More specifically, pivot point (524) occurs at the location where underside surface (520) of body (517) and underside surface (522) of placement tip (519) meet. With this configuration, end effector (512) comprises a placement tip (519) extending from the distal end of upper jaw (514). Placement tip (519) comprises a first angle ($\theta 3$) with respect to the axis of body (517) of upper jaw (514), or longitudinal axis (LA1), when end effector (512) is in the open position. Placement tip (519) further comprises a second angle ($\theta 4$) with respect to the axis of body (517) of upper jaw (514), when end effector (512) is in the closed position, and second angle ($\theta 4$) differs from first angle ($\theta 3$).

In view of the teachings herein, various ways to modify end effector (512) and the deflection of placement tip (519) such that other angles are achieved for second angle ($\theta 4$) when end effector (512) is in a closed position will be apparent to those of ordinary skill in the art in view of the teachings herein. By way of example only, and not limitation, one such modification would be to alter the relationship of the contact that placement tip (519) makes with lower jaw (516) when end effector (512) is closed. In the present example, lower jaw (516) comprises a nose portion (526) at a distal end of lower jaw (516). Furthermore, nose portion (526) comprises a top surface (528) that defines a plane having a slope relative to a longitudinal axis (LA2) of lower jaw (516). This slope can impact the deflection of the placement tip (519) thereby causing changes in the second angle ($\theta 4$). By way of another example only, and not limitation, another such modification would be to include features on top surface (528) that direct and/or impact the deflection of the placement tip (519) thereby causing changes in the second angle (θ4).

In some versions, upper jaw (514) comprises an anvil (518) similar to anvils (18, 218, 318) as described above. In such versions, anvil (518) comprises body (517) and placement tip (519). Also in such versions, opposite anvil (518), lower jaw (516) comprises a staple cartridge (537) with nose portion (526). With this configuration, end effector (512) comprises placement tip (519) extending from the distal end of anvil (518). Placement tip (519) comprises a first angle (θ3) with respect to anvil (518) axis or longitudinal axis (LA1) when end effector (512) is in the open position. Placement tip (519) further comprises a second angle (θ4) with respect to anvil (518) axis or longitudinal axis (LA1) when end effector (512) is in the closed position, and second angle (θ4) differs from first angle (θ3) as described above. In some other versions, the location of anvil (518) and cartridge (537) can be switched such that lower jaw (516) comprises anvil (518) while upper jaw (514) comprises staple cartridge (537).

B. Exemplary Angles with Deflection by Tissue

Figure 18:
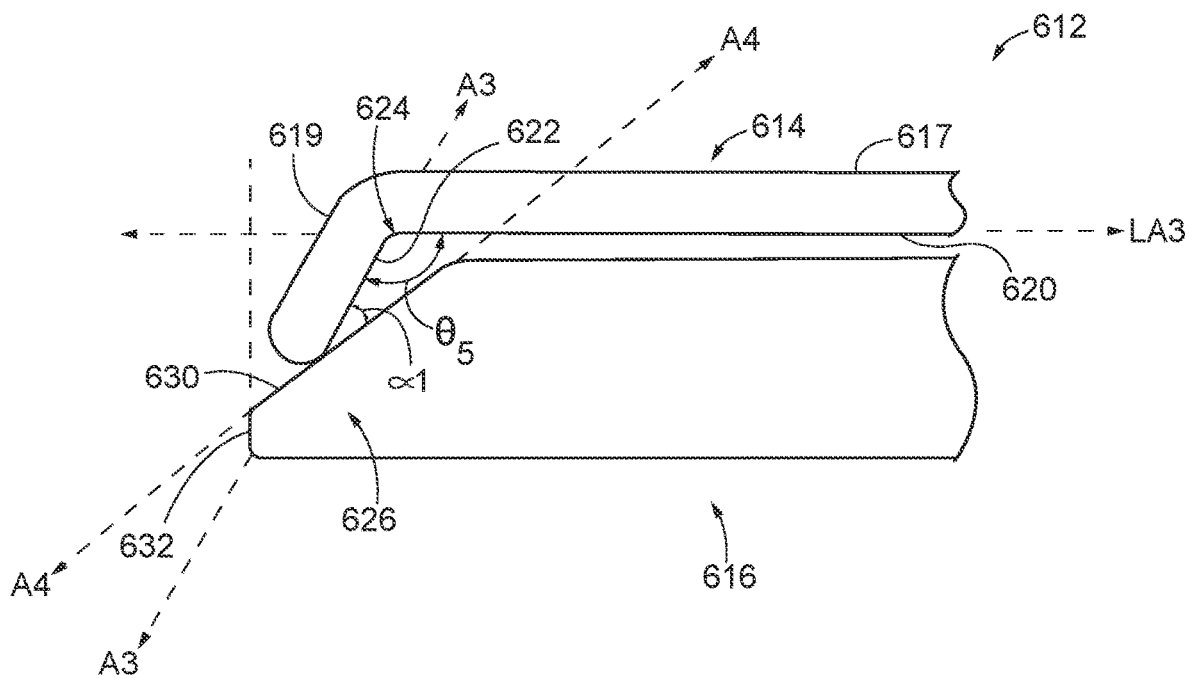
FIG. 18 depicts an enlarged side view of a distal portion of an alternative version of an end effector, shown in a closed and unloaded position and having an upper jaw with placement tip that forms a first angle with a nose portion of a lower jaw.
Figure 19:
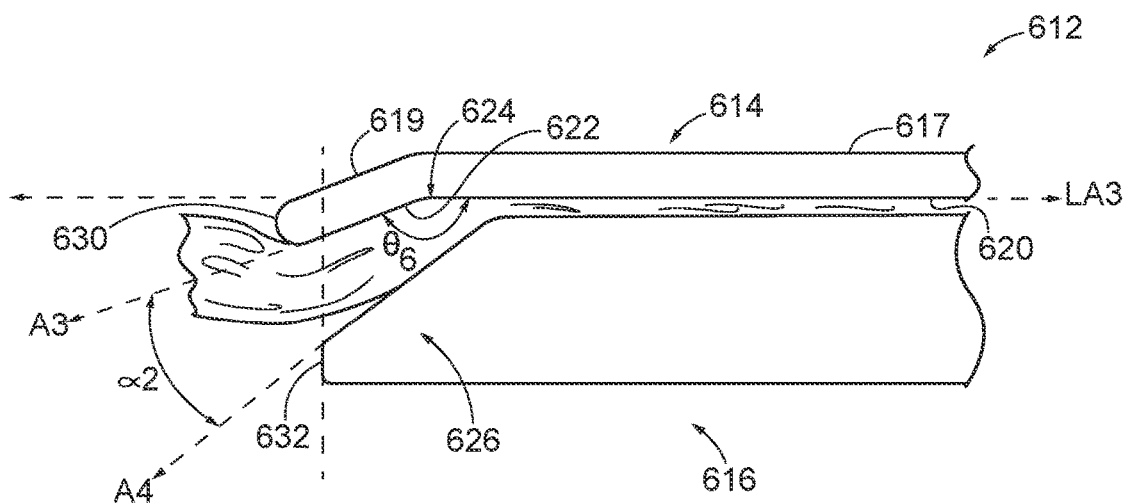
FIG. 19 depicts an enlarged side view of the distal portion of the end effector of FIG. 18, shown in a closed and loaded position and having the placement tip forming a second angle with the nose portion of the lower jaw.

Referring now to FIGS. 18 and 19, an enlarged view of an end effector (612) is shown. End effector (612) is configured for use with instruments (10, 310) and/or for robotic use as described above. End effector (612) comprises an upper jaw (614) and a lower jaw (616). In the present example, upper jaw (614) comprises a body (617) having placement tip (619) that is bent or angled and elastically deformable. Body (617), excluding the placement tip (619), defines a longitudinal axis (LA3) that extends along an underside surface (620) of body (617). Placement tip (619) defines another axis (A3) that extends along an underside surface (622) of placement tip (619). Furthermore, in the present example, lower jaw (616) comprises a tapered nose portion (626) at a distal end of lower jaw (616). Nose portion (626) defines an axis (A4) that extends along a top surface (628) of nose portion (626).

As shown in FIG. 18, end effector (612) is in an unloaded state with no tissue or other object between upper jaw (614) and lower jaw (616). A third angle (θ5) is defined by the intersection of longitudinal axis (LA3) of body (617) and axis (A3) of placement tip (619). Stated another way, third angle (θ5) is defined by the intersection of a plane extending along underside surface (620) of body (617) and a plane extending along underside surface (622) of placement tip (619) when end effector (612) is in an unloaded state. Similarly, when end effector (612) is in an unloaded state with no tissue or other object between upper jaw (614) and lower jaw (616) as shown in FIG. 18, a fifth angle (α1) is defined by the intersection of axis (A3) of placement tip (619) and axis (A4) of nose portion (626). Stated another way, fifth angle (α1) is defined by the intersection of a plane extending along underside surface (622) of placement tip (619) and a plane extending along top surface (628) of nose portion (626) when end effector (612) is in an unloaded state. As also shown in the present example of FIG. 18, with end effector (612) closed and in an unloaded state, an end (630) of placement tip (619) is located proximal to an end (632) of nose portion (626).

As shown in FIG. 19, end effector (612) has been moved to a closed position and loaded state with tissue between upper jaw (614) and lower jaw (616) of end effector (612). With tissue between jaws (614, 616) and the elastically deformable nature of placement tip (619), placement tip (619) deflects from its position relative to body (617). In this deflected position or state, a fourth angle (θ6) is defined by the intersection of longitudinal axis (LA3) of body (617) and axis (A3) of placement tip (619). Stated another way, fourth angle (θ6) is defined by the intersection of a plane extending along underside surface (620) of body (617) and a plane extending along underside surface (622) of placement tip (619) when end effector (612) is in a loaded state. Similarly, when end effector (612) is in the loaded state with tissue between upper jaw (614) and lower jaw (616) as shown in FIG. 19, a sixth angle (α2) is defined by the intersection of axis (A3) of placement tip (619) and axis (A4) of nose portion (626). Stated another way, sixth angle (α2) is defined by the intersection of a plane extending along underside surface (622) of placement tip (619) and a plane extending along top surface (628) of nose portion (626) when end effector (612) is in a loaded state. As also shown in the present example of FIG. 19, with end effector (612) closed and in a loaded state, end (630) of placement tip (619) is located distal to end (632) of nose portion (626).

With the deflection of placement tip (619) in the loaded state of FIG. 19 versus the unloaded state of FIG. 18, fourth angle (θ6) is not the same as third angle (θ5). For instance, with the illustrated deflection in FIG. 19, the tissue contacts the underside of placement tip (619) such that placement tip (619) pivots upward away from lower jaw (616) such that the fourth angle (θ6) is greater than the third angle (θ5). In the present example, end effector (612) defines a pivot point (624) about which placement tip (619) pivots relative to body (617). More specifically, pivot point (624) occurs at the location where underside surface (620) of body (617) and underside surface (622) of placement tip (619) meet. With this configuration, end effector (612) comprises a placement tip (619) extending from the distal end of upper jaw (614). Placement tip (619) comprises a third angle (θ5) with respect to the axis of body (617) of upper jaw (614), or longitudinal axis (LA3), when end effector (612) is in the closed and unloaded state. Placement tip (619) further comprises a fourth angle (θ6) with respect to the axis of body (617) of upper jaw (614), when end effector (612) is in the closed position and loaded state, and fourth angle (θ6) differs from third angle (θ5). Similarly with this configuration, end effector (612) comprises placement tip (619) having an undeflected state and a deflected state. In the undeflected state placement tip (619) and nose portion (626) define fifth angle (α1), and in the deflected state placement tip (619) and nose portion (626) define sixth angle (α2) that differs from fifth angle (α1).

In view of the teachings herein, various ways to modify end effector (612) and the deflection of placement tip (619) such that other angles are achieved for fourth angle (θ6) and sixth angle (α2) when end effector (612) is in a closed and loaded state will be apparent to those of ordinary skill in the art in view of the teachings herein. By way of example only, and not limitation, one such modification would be to alter the taper of nose portion (626) so that axis (A4) that extends along top surface (628) of nose portion (626) is steeper or shallower. By way of another example only, and not limitation, another such modification would be to include features on top surface (628) that direct the tissue held between the nose portion (626) and placement tip (619) to alter the force applied to placement tip (619) and thereby the deflection of placement tip (619) to cause changes in fourth angle (θ6) and sixth angle (α2) when end effector (612) is in a closed and loaded state.

In some versions, upper jaw (614) comprises an anvil (618) similar to anvils (18, 218, 318) as described above. In such versions, anvil (618) comprises body (617) and placement tip (619). Also in such versions, opposite anvil (618), lower jaw (616) comprises a staple cartridge (637) with nose portion (626). With this configuration, end effector (612) comprises placement tip (619) extending from the distal end of anvil (618). Placement tip (619) comprises a third angle ($\theta 5$) with respect to anvil (618) axis or longitudinal axis (LA3) when end effector (612) is in the closed and unloaded state. Placement tip (619) further comprises a fourth angle ($\theta 6$) with respect to anvil (618) axis or longitudinal axis (LA3) when end effector (612) is in the closed and loaded state, and fourth angle ($\theta 6$) differs from third angle ($\theta 5$) as described above. Similarly with this configuration, end effector (612) comprises placement tip (619) extending from the distal end of anvil (618), and nose portion (619) at a distal end of cartridge (637), where end effector (612) has an undeflected state and a deflected state. In the undeflected state placement tip (619) of anvil (618), and nose portion (626) of cartridge (637), define fifth angle ($\alpha 1$). In the deflected state placement tip (619) of anvil (618), and nose portion (626) of cartridge (637) define sixth angle ($\alpha 2$) that differs from fifth angle ($\alpha 1$). In some other versions, the location of anvil (618) and cartridge (637) can be switched such that lower jaw (616) comprises anvil (618) while upper jaw (614) comprises staple cartridge (637).

C. Exemplary Tip Positions in Deflected and Non-Deflected States

As described above with respect to FIGS. 18 and 19, placement tip (619) is configured to deflect when end effector (612) is loaded, and such deflection occurs in a manner where end (630) of placement tip (619) changes its relative placement or location with respect to end (632) of nose portion (626) of cartridge (637). As shown in FIGS. 18 and 19, end (630) is proximal to end (632) when end effector (612) is unloaded such that there is an absence of tissue between upper jaw (614) and lower jaw (616). And when end effector (612) is loaded with tissue between upper jaw (614) and lower jaw (616), end (630) moves distally such that end (630) is distal to end (632).

Figure 20:
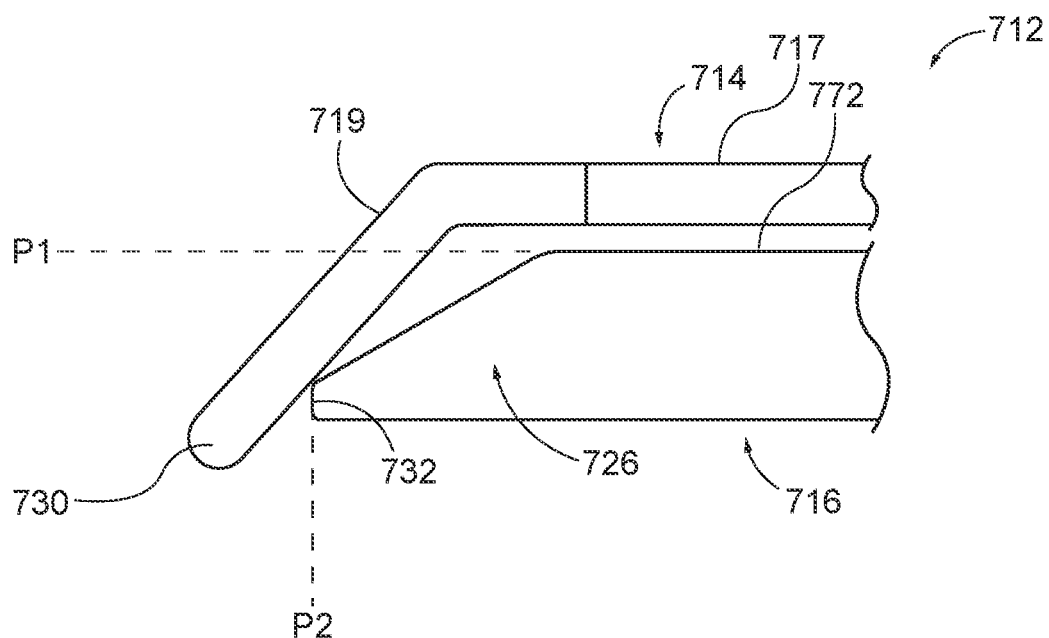
FIG. 20 depicts an enlarged side view of a distal portion of an alternative version of an end effector, shown in a closed position with a distal end of a placement tip of an upper jaw being located relative to a deck and a distal end of a lower jaw.

Referring now to FIG. 20, an enlarged view of an end effector (712) is shown. End effector (712) is configured for use with instruments (10, 310) and/or for robotic use as described above. End effector (712) comprises upper jaw (714) and lower jaw (716). Lower jaw (716) comprises nose portion (726) and end (732). Lower jaw (716) further comprises deck (772). Upper jaw (714) comprises a body (717) and a placement tip (719). Placement tip (719) has a bent or angled configuration and is elastically deformable as described above. Placement tip (719) comprises end (730) at its distal-most portion.

As shown in FIG. 20, a first reference plane (P1) is defined by deck (772), and generally extends parallel with a longitudinal axis of lower jaw (716). A second reference plane (P2) passes through end (732) of nose portion (726) such that second reference plane (P2) is orthogonal to first reference plane (P1). As shown in FIG. 20, the location or placement of end (732) of placement tip (719) can be shown and described relative to first reference plane (P1) and second reference plane (P2). In other words, the location or placement of end (730) of placement tip (719) can be described as being proximal to, even with, or distal to end (732) of nose portion (726) of lower jaw (716) as illustrated by second reference plane (P2). At the same time, the location or placement of end (730) of placement tip (719) can be described as being above, even with, or below deck (772) of lower jaw (716) as illustrated by first reference plane (P1).

Figure 21:
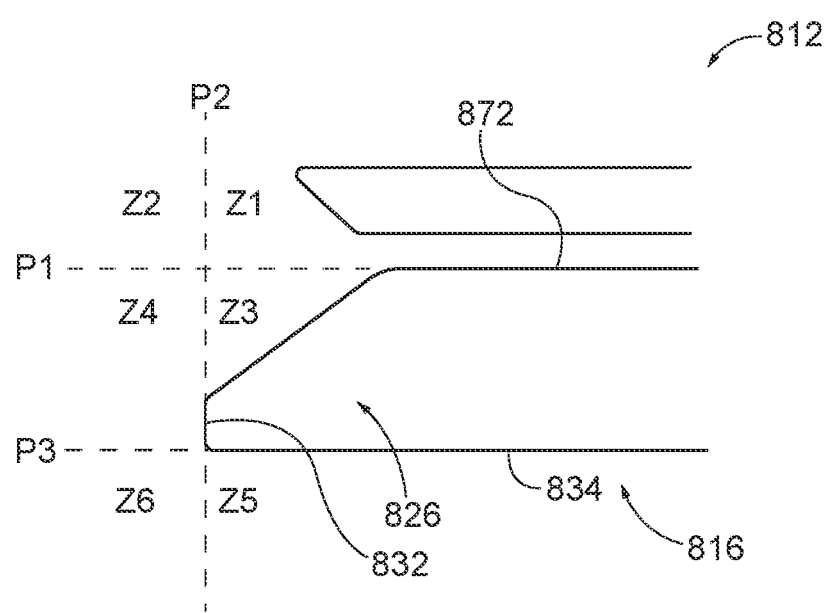
FIG. 21 depicts an enlarged side view of a distal portion of an alternative version of an end effector, shown in a closed position and with zones defined by a lower jaw with a distal end of a placement tip of an upper jaw being located in a first zone.

Referring now to FIG. 21, an enlarged view of another end effector (812) is shown with reference markings that define multiple zones that can be used to describe the location or placement of the end of the placement tip of an exemplary end effector. End effector (812) is configured for use with instruments (10, 310) and/or for robotic use as described above. As with end effector (712) and FIG. 20, end effector (812) of FIG. 21 also comprises first reference plane (P1) and second reference plane (P2). Additionally, a third reference plane (P3) is defined by and extends along a bottom surface (834) of lower jaw (816). Third reference plane (P3) in the present example is parallel with first reference plane (P1) and also orthogonal to second reference plane (P2). With this configuration, as shown in FIG. 21, six zones are defined by the intersections of first and third reference planes (P1, P3) with second reference plane (P2).

A first zone (Z1) is shown as the region above deck (872) of lower jaw (816) (corresponding with first reference plane (P1)) and proximal to end (832) of nose portion (826) (corresponding with second reference plane (P2)). A second zone (Z2) is shown as the region above deck (872) of lower jaw (816) (corresponding with first reference plane (P1)) and distal to end (832) of nose portion (826) (corresponding with second reference plane (P2)). A third zone (Z3) is shown as the region below deck (872) of lower jaw (816) (corresponding with first reference plane (P1)) yet above bottom surface (834) of lower jaw (816) (corresponding with third reference plane (P3)), and proximal to end (832) of nose portion (826) (corresponding with second reference plane (P2)). A fourth zone (Z4) is shown as the region below deck (872) of lower jaw (816) (corresponding with first reference plane (P1)) yet above bottom surface (834) of lower jaw (816) (corresponding with third reference plane (P3)), and distal to end (832) of nose portion (826) (corresponding with second reference plane (P2)). A fifth zone (Z5) is shown as the region below bottom surface (834) of lower jaw (816) (corresponding with third reference plane (P3)), and proximal to end (832) of nose portion (826) (corresponding with second reference plane (P2)). A sixth zone (Z6) is shown as the region below bottom surface (834) of lower jaw (816) (corresponding with third reference plane (P3)), and distal to end (832) of nose portion (826) (corresponding with second reference plane (P2)).

Figure 22A:
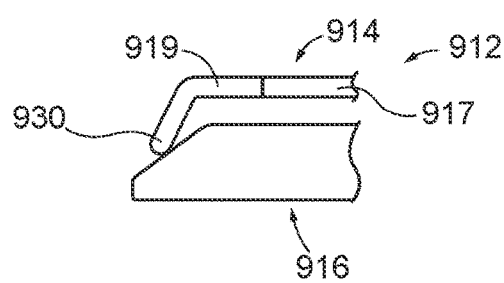
FIG. 22A depicts an enlarged side view of a distal portion of an alternative version of an end effector, shown in a closed position and with a distal end of a placement tip of an upper jaw being located in a third zone as shown in FIG. 21.

Using this reference system, several exemplary end effectors will now be described that illustrate various locations or placements for the end of the placement tip when the end effector is in a closed and unloaded state. Referring to FIG. 22A, an enlarged view of another end effector (912) is shown in a closed and unloaded state. End effector (912) is configured for use with instruments (10, 310) and/or for robotic use as described above. End effector (912) comprises an upper jaw (914) and a lower jaw (916). Upper jaw (914) comprises a body (917) and a placement tip (919). At its distal-most portion, placement tip (919) comprises an end (930). As shown, placement tip (919) has a bent or angled configuration. With the illustrated configuration, placement tip (919) extends through first zone (Z1), and the location of end (930) of placement tip (919) is in third zone (Z3). In view of the teachings herein, it will be apparent to those of ordinary skill in the art that when end effector (912) is in a closed and loaded state that the location of end (930) of placement tip (919) may deflect yet remain in third zone (Z3). However, it will also be apparent to those of ordinary skill in the art in view of the teachings herein that placement tip (919) may deflect such that end (930) of placement tip (919) changes its location in the closed and loaded state to another one of the zones.

Figure 22B:
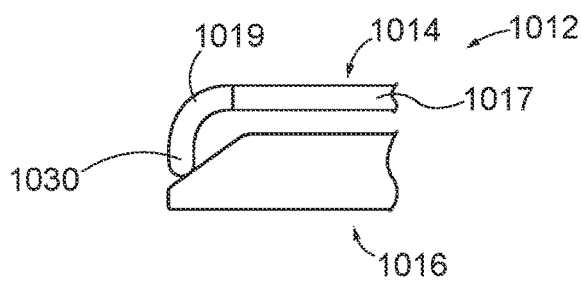
FIG. 22B depicts an enlarged side view of a distal portion of an alternative version of an end effector, shown in a closed position and with a distal end of a curved placement tip of an upper jaw being located in a third zone as shown in FIG. 21.

Referring now to FIG. 22B, an enlarged view of another end effector (1012) is shown in a closed and unloaded state. End effector (1012) is configured for use with instruments (10, 310) and/or for robotic use as described above. End effector (1012) comprises an upper jaw (1014) and a lower jaw (1016). Upper jaw (1014) comprises a body (1017) and a placement tip (1019). At its distal-most portion, placement tip (1019) comprises an end (1030). As shown, placement tip (1019) has a curved configuration. With the illustrated configuration, placement tip (1019) extends through first zone (Z1), and the location of end (1030) of placement tip (1019) is in third zone (Z3). In view of the teachings herein, it will be apparent to those of ordinary skill in the art that when end effector (1012) is in a closed and loaded state that the location of end (1030) of placement tip (1019) may deflect yet remain in third zone (Z3). However, it will also be apparent to those of ordinary skill in the art in view of the teachings herein that placement tip (1019) may deflect such that end (1030) of placement tip (1019) changes its location in the closed and loaded state to another one of the zones.

Figure 22C:
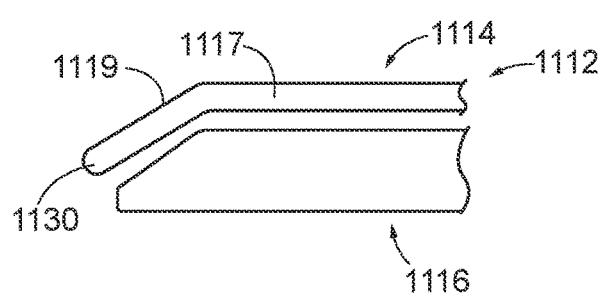
FIG. 22C depicts an enlarged side view of a distal portion of an alternative version of an end effector, shown in a closed position and with a distal end of a placement tip of an upper jaw being located in a fourth zone as shown in FIG. 21.

Referring now to FIG. 22C, an enlarged view of another end effector (1112) is shown in a closed and unloaded state. End effector (1112) is configured for use with instruments (10, 310) and/or for robotic use as described above. End effector (1112) comprises an upper jaw (1114) and a lower jaw (1116). Upper jaw (1114) comprises a body (1117) and a placement tip (1119). At its distal-most portion, placement tip (1119) comprises an end (1130). As shown, placement tip (1119) has a bent or angled configuration. With the illustrated configuration, placement tip (1119) extends through first and third zones (Z1, Z3) and the location of end (1130) of placement tip (1119) is in fourth zone (Z4). In view of the teachings herein, it will be apparent to those of ordinary skill in the art that when end effector (1112) is in a closed and loaded state that the location of end (1130) of placement tip (1119) may deflect yet remain in fourth zone (Z4). However, it will also be apparent to those of ordinary skill in the art in view of the teachings herein that placement tip (1119) may deflect such that end (1130) of placement tip (1119) changes its location in the closed and loaded state to another one of the zones.

Figure 22D:
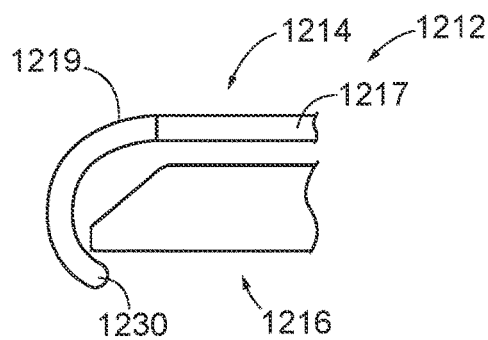
FIG. 22D depicts an enlarged side view of a distal portion of an alternative version of an end effector, shown in a closed position and with a distal end of a curved placement tip of an upper jaw being located in a fifth zone as shown in FIG. 21.

Referring now to FIG. 22D, an enlarged view of another end effector (1212) is shown in a closed and unloaded state. End effector (1212) is configured for use with instruments (10, 310) and/or for robotic use as described above. End effector (1212) comprises an upper jaw (1214) and a lower jaw (1216). Upper jaw (1214) comprises a body (1217) and a placement tip (1219). At its distal-most portion, placement tip (1219) comprises an end (1230). As shown, placement tip (1219) has a curved configuration. With the illustrated configuration, placement tip (1219) extends through first, second, third, fourth, and sixth zones (Z1, Z2, Z3, Z4, Z6) and the location of end (1230) of placement tip (1219) is in fifth zone (Z5). Out of the six total zones, placement tip (1230) passes through all of them, albeit third zone (Z3) is substantially void of placement tip (1230). In view of the teachings herein, it will be apparent to those of ordinary skill in the art that when end effector (1212) is in a closed and loaded state that the location of end (1230) of placement tip (1219) may deflect yet remain in fifth zone (Z5). However, it will also be apparent to those of ordinary skill in the art in view of the teachings herein that placement tip (1219) may deflect such that end (1230) of placement tip (1219) changes its location in the closed and loaded state to another one of the zones.

Figure 22E:
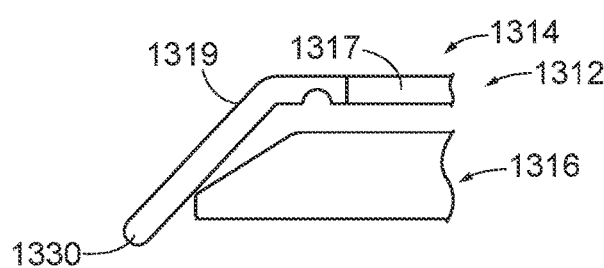
FIG. 22E depicts an enlarged side view of a distal portion of an alternative version of an end effector, shown in a closed position and with a distal end of a placement tip of an upper jaw being located in a sixth zone as shown in FIG. 21.

Referring now to FIG. 22E, an enlarged view of another end effector (1312) is shown in a closed and unloaded state. End effector (1312) is configured for use with instruments (10, 310) and/or for robotic use as described above. End effector (1312) comprises an upper jaw (1314) and a lower jaw (1316). Upper jaw (1314) comprises a body (1317) and a placement tip (1319). At its distal-most portion, placement tip (1319) comprises an end (1330). As shown, placement tip (1319) has a bent or angled configuration. With the illustrated configuration, placement tip (1319) extends through first, third, and fourth zones (Z1, Z3, Z4) and the location of end (1330) of placement tip (1319) is in sixth zone (Z6). In view of the teachings herein, it will be apparent to those of ordinary skill in the art that when end effector (1312) is in a closed and loaded state that the location of end (1330) of placement tip (1319) may deflect yet remain in sixth zone (Z6). However, it will also be apparent to those of ordinary skill in the art in view of the teachings herein that placement tip (1319) may deflect such that end (1330) of placement tip (1319) changes its location in the closed and loaded state to another one of the zones.

Figure 22F:
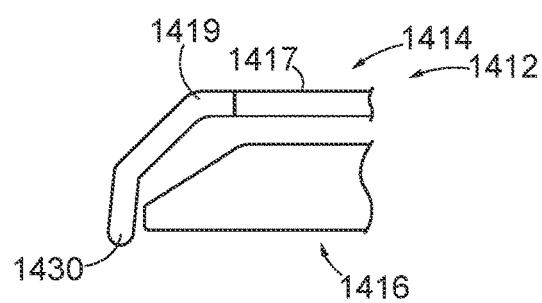
FIG. 22F depicts an enlarged side view of a distal portion of an alternative version of an end effector, shown in a closed position and with a distal end of a multi-angled placement tip of an upper jaw being located in a sixth zone as shown in FIG. 21.

Referring now to FIG. 22F, an enlarged view of another end effector (1412) is shown in a closed and unloaded state. End effector (1412) is configured for use with instruments (10, 310) and/or for robotic use as described above. End effector (1412) comprises an upper jaw (1414) and a lower jaw (1416). Upper jaw (1414) comprises a body (1417) and a placement tip (1419). At its distal-most portion, placement tip (1419) comprises an end (1430). As shown, placement tip (1419) has a multi-angled configuration. With the illustrated configuration, placement tip (1419) extends through first, third, and fourth zones (Z1, Z3, Z4) and the location of end (1430) of placement tip (1419) is in sixth zone (Z6). In view of the teachings herein, it will be apparent to those of ordinary skill in the art that when end effector (1412) is in a closed and loaded state that the location of end (1430) of placement tip (1419) may deflect yet remain in sixth zone (Z6). However, it will also be apparent to those of ordinary skill in the art in view of the teachings herein that placement tip (1419) may deflect such that end (1430) of placement tip (1419) changes its location in the closed and loaded state to another one of the zones.

Figure 22G:
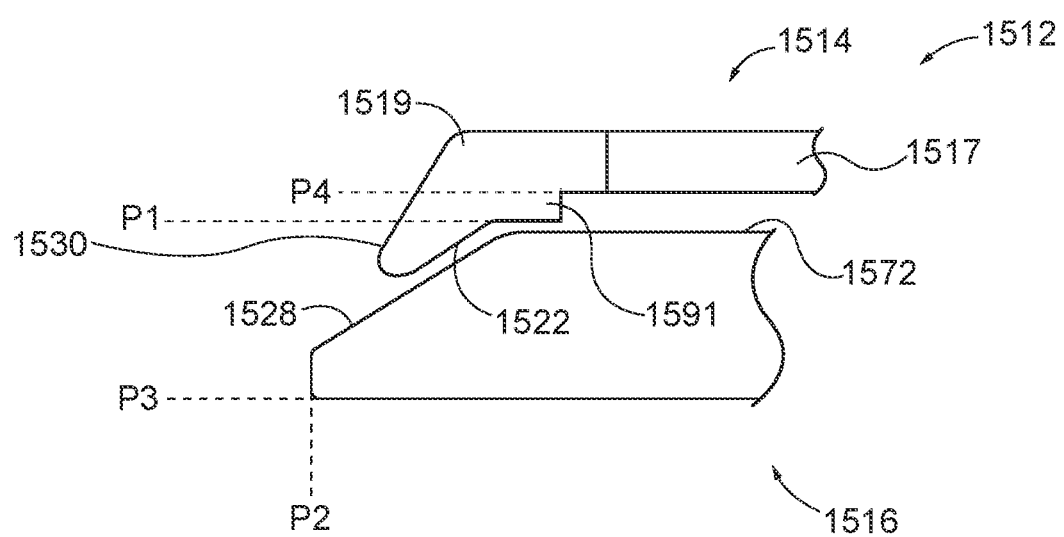
FIG. 22G depicts an enlarged side view of a distal portion of an alternative version of an end effector, shown in a closed position and with a distal end of a placement tip of an upper jaw being located in a third zone as shown in FIG. 21, and the placement tip configured with a profile of an underside surface that corresponds with a profile of a taper of the nose portion of a lower jaw.

Referring now to FIG. 22G, an enlarged view of another end effector (1512) is shown in a closed and unloaded state. End effector (1512) is configured for use with instruments (10, 310) and/or for robotic use as described above. End effector (1512) comprises an upper jaw (1514) and a lower jaw (1516). Upper jaw (1514) comprises a body (1517) and a placement tip (1519). At its distal-most portion, placement tip (1519) comprises an end (1530). As shown, placement tip (1519) has a bent or angled configuration. At its proximal end, placement tip (1519) comprises a step (1591) such that body (1517) is offset from step (1591) of placement tip (1519). With the illustrated configuration, placement tip (1519) extends through first zone (Z1) and the location of end (1530) of placement tip (1519) is in third zone (Z3). In view of the teachings herein, it will be apparent to those of ordinary skill in the art that when end effector (1512) is in a closed and loaded state that the location of end (1530) of placement tip (1519) may deflect yet remain in third zone (Z3). However, it will also be apparent to those of ordinary skill in the art in view of the teachings herein that placement tip (1519) may deflect such that end (1530) of placement tip (1519) changes its location in the closed and loaded state to another one of the zones.

As shown in FIG. 22G, end effector (1512) defines a fourth reference plane (P4) based on the offset of body (1517) from step (1591) of placement tip (1519). Also, placement tip (1519) comprises an underside surface (1522) that matches the profile of top surface (1528) and deck (1572) of lower jaw (1516). Placement tip (1519) defines pivot point (1524) where underside surface (1522) transitions from matching the profile of top surface (1528) of lower jaw (1516) to matching deck (1572) of lower jaw (1516). As shown in the illustrated version, end effector (1512) defines a first distance (D1) as extending from pivot point (1524) proximally to the proximal-most end of step (1591). First distance (D1) can be consider as representing the length of placement tip (1519) that overlaps deck (1572) of lower jaw (1516). In view of the teaching herein, various ways to modify or alter end effector (1512) and first distance (D1) to achieve greater or smaller overlaps of placement tip (1519) and deck (1572) will be apparent to those of ordinary skill in the art.

The above paragraphs describe a reference system where various reference planes are used to define zones relative to an end effector. Specifically the various reference planes are relative to an end effector's lower jaw's deck, distal-most end, and bottom surface. This reference system is applicable to other versions of end effectors shown and described herein, other than those described above in FIGS. 22A-22G. For example, it is clear from FIG. 17 that end effector (512) comprises placement tip (519) that presents its distal-most end in third zone (Z3). Similarly, FIG. 18 illustrates that end effector (612) comprises placement tip (619) that presents its distal-most end also in third zone (Z3). With respect to end effectors (512, 612) and FIGS. 17 and 18, both end effectors (512, 612) are shown in closed and unloaded states. Referring to FIG. 19, end effector (612) is shown in a closed and loaded state. As illustrated, with end effector (612) in a closed and loaded state, placement tip (619) deflects such that the distal-most end of placement tip (619) is located mostly in second zone (Z2) with a smaller portion located in fourth zone (Z4). In view of the teachings herein, various ways to configure an end effector to locate an end of a placement tip in a desired position under various conditions, i.e. open/closed and loaded/unloaded, will be apparent to those of ordinary skill in the art.

D. Exemplary Shapes for Elastically Deformable Placement Tips

As described above, placement tips for end effectors can have a bent or angled configuration as well as a curved configuration. This is shown in the several side views of FIGS. 22A-22G for instance. In combination with these various options for placement tips of an end effector, further options for the shape of the placement tip exist. As will be described below, placement tips can be configured with various distal end profiles, width profiles, and underside surface geometries. It should be understood that the various shapes described below related to distal end profile, width profile, and underside surface geometry can be combined in a single placement tip. For instance any of the distal end profiles shown and described can be used in a placement tip having any of the width profiles shown and described, and further such a placement tip can have any of the underside surface geometries shown and described.

1. Distal End Profiles

Figure 23A:
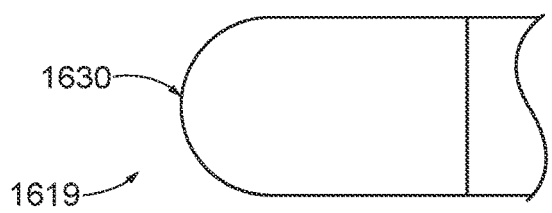
FIG. 23A depicts an enlarged top view of a placement tip of an alternative version of an end effector, with the placement tip having a distal end with a round profile.

FIGS. 23A-23F depict exemplary enlarged placement tip portions that show various distal end profiles for the placement tip. Referring to FIG. 23A, an end effector comprises a placement tip (1619). As shown in the top view of FIG. 23A, placement tip (1619) comprises a distal end (1630) having a round profile. Placement tip (1619) is configurable such that it may be positioned on either an upper jaw or lower jaw of the end effector. Furthermore, placement tip (1619) is configurable such that it may be part of an anvil or part of a staple cartridge. In view of the teachings herein, it will be apparent to those of ordinary skill in the art that this round distal end profile of placement tip (1619) can be used with any of the placement tips of the end effectors described herein.

Figure 23B:
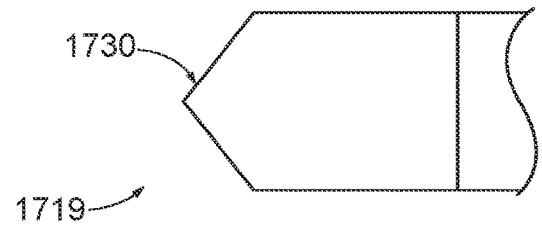
FIG. 23B depicts an enlarged top view of a placement tip of an alternative version of an end effector, with the placement tip having a distal end with an angled and pointed profile.

FIG. 23B depicts an end effector comprising a placement tip (1719). As shown in the top view of FIG. 23B, placement tip (1719) comprises a distal end (1730) having an angled and pointed profile. In this example, because placement tip (1719) is comprises of an elastomeric and deflectable material, placement tip (1719) is still configured as an atraumatic tip despite its pointed profile. Placement tip (119) is configurable such that it may be positioned on either an upper jaw or lower jaw of the end effector. Furthermore, placement tip (119) is configurable such that it may be part of an anvil or part of a staple cartridge. In view of the teachings herein, it will be apparent to those of ordinary skill in the art that this angled and pointed distal end profile of placement tip (119) can be used with any of the placement tips of the end effectors described herein.

Figure 23C:
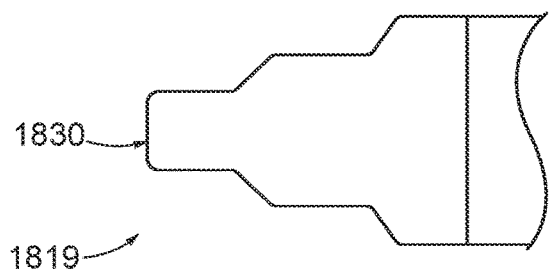
FIG. 23C depicts an enlarged top view of a placement tip of an alternative version of an end effector, with the placement tip having a distal end with a toothed profile.

FIG. 23C depicts an end effector comprising a placement tip (1819). As shown in the top view of FIG. 23C, placement tip (1819) comprises a distal end (1830) having a toothed profile. Placement tip (1819) is configurable such that it may be positioned on either an upper jaw or lower jaw of the end effector. Furthermore, placement tip (1819) is configurable such that it may be part of an anvil or part of a staple cartridge. In view of the teachings herein, it will be apparent to those of ordinary skill in the art that this toothed distal end profile of placement tip (1819) can be used with any of the placement tips of the end effectors described herein.

Figure 23D:
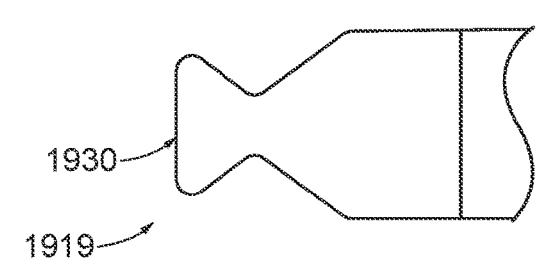
FIG. 23D depicts an enlarged top view of a placement tip of an alternative version of an end effector, with the placement tip having a distal end with a flared profile.

FIG. 23D depicts an end effector comprising a placement tip (1919). As shown in the top view of FIG. 23D, placement tip (1919) comprises a distal end (1930) having a flared profile. Placement tip (1919) is configurable such that it may be positioned on either an upper jaw or lower jaw of the end effector. Furthermore, placement tip (1919) is configurable such that it may be part of an anvil or part of a staple cartridge. In view of the teachings herein, it will be apparent to those of ordinary skill in the art that this flared distal end profile of placement tip (1919) can be used with any of the placement tips of the end effectors described herein.

Figure 23E:
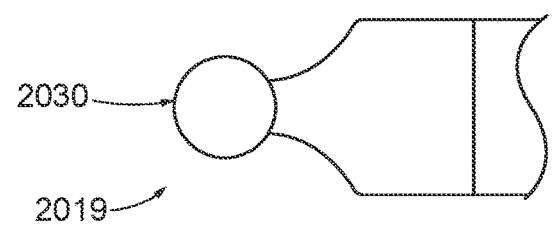
FIG. 23E depicts an enlarged top view of a placement tip of an alternative version of an end effector, with the placement tip having a distal end with an orb profile.

FIG. 23E depicts an end effector comprising a placement tip (2019). As shown in the top view of FIG. 23E, placement tip (2019) comprises a distal end (2030) having a orb profile. Placement tip (2019) is configurable such that it may be positioned on either an upper jaw or lower jaw of the end effector. Furthermore, placement tip (2019) is configurable such that it may be part of an anvil or part of a staple cartridge. In view of the teachings herein, it will be apparent to those of ordinary skill in the art that this orb distal end profile of placement tip (2019) can be used with any of the placement tips of the end effectors described herein.

Figure 23F:
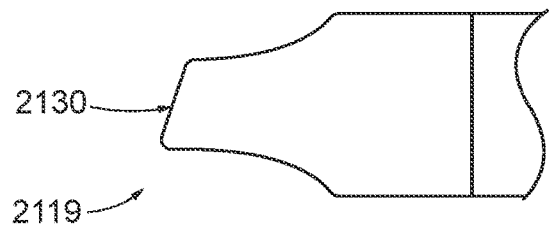
FIG. 23F depicts an enlarged top view of a placement tip of an alternative version of an end effector, with the placement tip having a distal end with an asymmetric profile.

FIG. 23F depicts an end effector comprising a placement tip (2119). As shown in the top view of FIG. 23F, placement tip (2119) comprises a distal end (2130) having a asymmetric profile. In this manner, end (2130) extends distally longer on one side than the other such that end (2130) is angled. Placement tip (2119) is configurable such that it may be positioned on either an upper jaw or lower jaw of the end effector. Furthermore, placement tip (2119) is configurable such that it may be part of an anvil or part of a staple cartridge. In view of the teachings herein, it will be apparent to those of ordinary skill in the art that this asymmetric distal end profile of placement tip (2119) can be used with any of the placement tips of the end effectors described herein. While several distal end profiles for placement tips of an end effector have been shown and described above, other distal end profiles for placement tips of an end effector will be apparent to those of ordinary skill in the art in view of the teachings herein.

2. Width Profiles

Figure 24A:
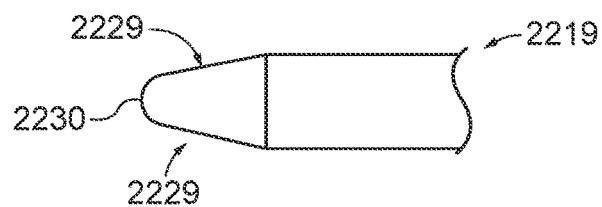
FIG. 24A depicts an enlarged top view of a placement tip of an alternative version of an end effector, with the placement tip having a width with an angled profile.

FIGS. 24A-24E depict exemplary enlarged placement tip portions that show various width profiles for the placement tip. Referring to FIG. 24A, an end effector comprises a placement tip (2219). As shown in the top view of FIG. 24A, placement tip (2219) comprises distal sides (2229) leading to distal end (2230) where distal sides (2229) define a width profile that is angled. Placement tip (2219) is configurable such that it may be positioned on either an upper jaw or lower jaw of the end effector. Furthermore, placement tip (2219) is configurable such that it may be part of an anvil or part of a staple cartridge. In view of the teachings herein, it will be apparent to those of ordinary skill in the art that this angled width profile of placement tip (2219) can be used with any of the placement tips of the end effectors described herein.

Figure 24B:
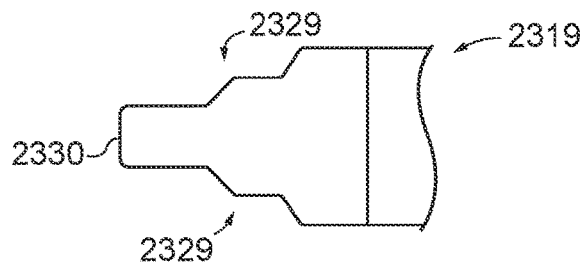
FIG. 24B depicts an enlarged top view of a placement tip of an alternative version of an end effector, with the placement tip having a width with a stepped profile.

FIG. 24B depicts an end effector comprising a placement tip (2319). As shown in the top view of FIG. 24B, placement tip (2319) comprises distal sides (2329) leading to distal end (2330) where distal sides (2329) define a width profile that is stepped. Placement tip (2319) is configurable such that it may be positioned on either an upper jaw or lower jaw of the end effector. Furthermore, placement tip (2319) is configurable such that it may be part of an anvil or part of a staple cartridge. In view of the teachings herein, it will be apparent to those of ordinary skill in the art that this stepped width profile of placement tip (2319) can be used with any of the placement tips of the end effectors described herein.

Figure 24C:
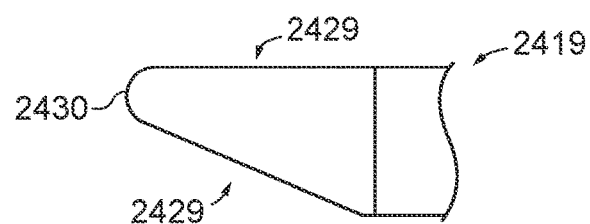
FIG. 24C depicts an enlarged top view of a placement tip of an alternative version of an end effector, with the placement tip having a width with a asymmetric profile.

FIG. 24C depicts an end effector comprising a placement tip (2419). As shown in the top view of FIG. 24C, placement tip (2419) comprises distal sides (2429) leading to distal end (2430) where distal sides (2429) define a width profile that is asymmetric such that distal sides (2429) are not symmetrically oriented, and in this instance are angled to varying degrees. Placement tip (2419) is configurable such that it may be positioned on either an upper jaw or lower jaw of the end effector. Furthermore, placement tip (2419) is configurable such that it may be part of an anvil or part of a staple cartridge. In view of the teachings herein, it will be apparent to those of ordinary skill in the art that this asymmetric width profile of placement tip (2419) can be used with any of the placement tips of the end effectors described herein.

Figure 24D:
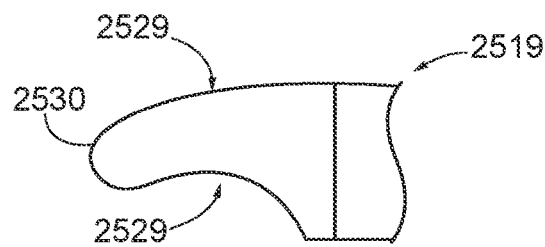
FIG. 24D depicts an enlarged top view of a placement tip of an alternative version of an end effector, with the placement tip having a width with a scallop tip-on-center profile.

FIG. 24D depicts an end effector comprising a placement tip (2519). As shown in the top view of FIG. 24D, placement tip (2519) comprises distal sides (2529) leading to distal end (2530) where distal sides (2529) define a width profile that is scalloped with distal end (2530) centered along the longitudinal axis of placement tip (2519). In this manner, one of distal sides (2529) has a curvature that is concave while the other has a curvature that is convex. Placement tip (2519) is configurable such that it may be positioned on either an upper jaw or lower jaw of the end effector. Furthermore, placement tip (2519) is configurable such that it may be part of an anvil or part of a staple cartridge. In view of the teachings herein, it will be apparent to those of ordinary skill in the art that this scalloped width profile of placement tip (2519) can be used with any of the placement tips of the end effectors described herein.

Figure 24E:
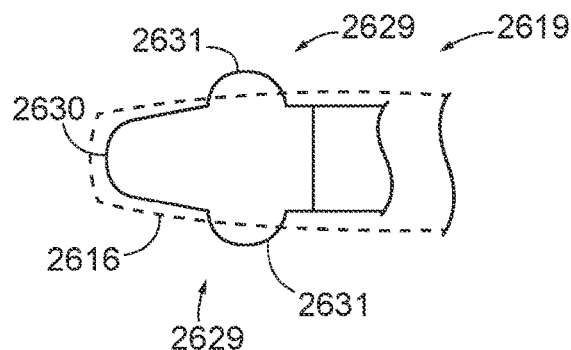
FIG. 24E depicts an enlarged top view of a placement tip of an alternative version of an end effector, with the placement tip having a width with a bump-out profile.

FIG. 24E depicts an end effector comprising a placement tip (2619). As shown in the top view of FIG. 24E, placement tip (2619) comprises distal sides (2629) leading to distal end (2630) where distal sides (2629) define a width profile having bump-outs or lateral protrusions (2631) on each side. In the illustrated version, a jaw (2616) of end effector opposite placement tip (2619) is shown in phantom. As shown in the present example, the bump-outs (2631) extend outward from jaw (2616), whereas the remaining width of placement tip (2619) is narrower than the width of jaw (2616). However, bump-outs (2631) are not required to extend out from the width of jaw (2616) in all versions. Where bump-outs (2631) do extend outward from jaw (2616), placement tip (2619) is configured to provide resistance when moving the instrument with the end effector and placement tip (2619) in and out of a site. Additionally, bump-outs (2631) are configured to dilate an aperture larger when placement tip (2619) passes therethrough. Placement tip (2619) is configurable such that it may be positioned on either an upper jaw or lower jaw of the end effector. Furthermore, placement tip (2619) is configurable such that it may be part of an anvil or part of a staple cartridge. In view of the teachings herein, it will be apparent to those of ordinary skill in the art that this width profile of placement tip (2619) having bump-outs (2631) on each side can be used with any of the placement tips of the end effectors described herein.

Figure 25:
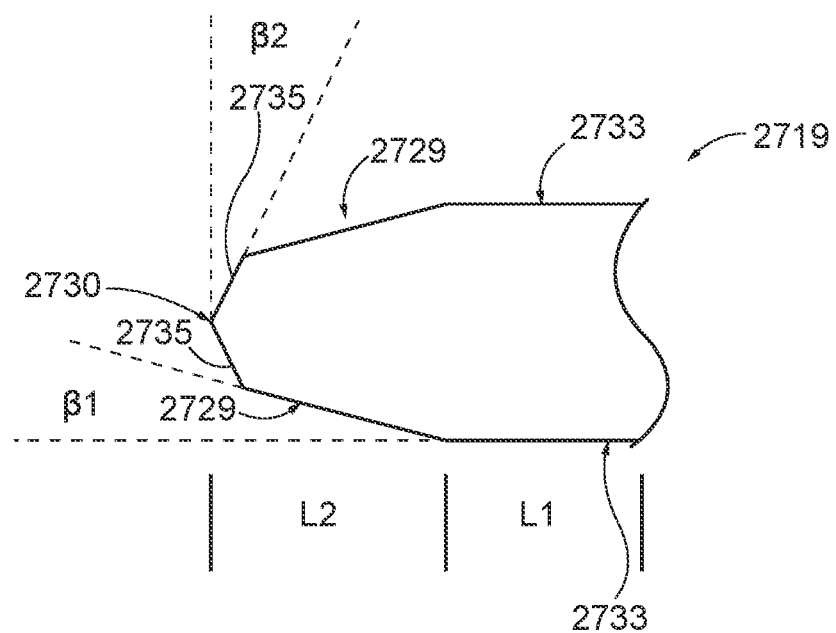
FIG. 25 depicts an enlarged top view of a placement tip of an alternative version of an end effector, with the placement tip having a distal end with an angled and pointed profile and with the placement tip having a width with an angled profile.

FIG. 25 depicts an enlarged top view of a placement tip (2719) of an end effector, with the placement tip (2719) having a distal end (2730) with an angled and pointed profile and with the placement tip (2719) having distal sides (2729) defining a width profile that angled. As described above, placement tip (2719) illustrates a combination of the angled and pointed distal end profile of placement tip (1719) of FIG. 23B, with the angled width profile of placement tip (2219) of FIG. 24A. In view of the teachings herein, and as further illustrated by this example, various combinations of distal end profiles and width profiles will be apparent to those of ordinary skill in the art.

Placement tip (2719) further illustrates the relationship between the profile at distal end (2730) compared to the width profile defined by distal sides (2729). As described above with respect to other examples, placement tips extend from a body of one of an upper jaw or lower jaw of an end effector. In the present example, placement tip (2719) is understood to have a shorter longitudinal dimension, or length, than the body of the jaw from which it extends. As shown in the illustrated version, placement tip (2719) can be understood to have a length characterized by the sum of a first length (L1) and a second length (L2). Although not shown to scale based on the wavy break line signifying that placement tip (2719) extends proximally further than shown, it should be understood that first length (L1) is substantially greater than second length (L2). When showing and describing the various distal end profiles and width profiles of placement tips above in FIGS. 23A-23F and 24A-24E, it should be understood that the distal end profiles as well as the width profiles defined by the distal sides are all included in the length of the placement tips that coincide with second length (L2).

Placement tip (2719) further illustrates an example where a plane defined by one of symmetrical distal sides (2729) in combination with another plane defined by one of a proximal sides (2733), form an angle (β1). In this example, as the width profile defined by distal sides (2729) becomes more angular or steeper, angle (β1) increases. When the width profile defined by distal sides (2729) becomes less angular, and hence closer to parallel with proximal sides (2733), angle (β1) decreases.

Placement tip (2719) also illustrates an example where a plane defined tangent to the distal-most portion of distal end (2730) in combination with a plane defined by one of sides (2735) of distal end (2730), forms an angle (β2). In this example, as the sides (2735) of distal end (2730) become more angular or steeper, angle (β2) increases. When the sides (2735) of distal end (2730) becomes less angular, and hence distal end (2730) more blunt, angle (β2) decreases.

3. Underside Surfaces

Figure 26A:
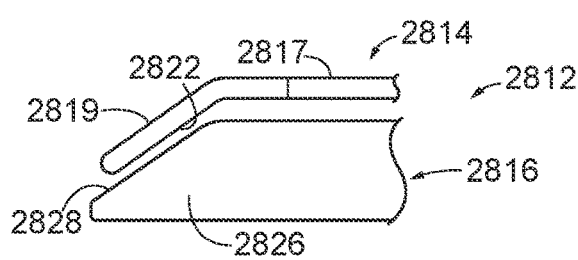
FIG. 26A depicts an enlarged side view of a distal portion of an alternative version of an end effector, with a placement tip of an upper jaw having an underside surface with a flat profile parallel with a profile of a nose portion of a lower jaw.

Now referring to the side views of FIGS. 26A-26E, various geometries for underside surfaces of placement tips are shown and described. In some instances underside surfaces of placement tips may be referred to as inner surfaces, and these terms should be understood to be interchangeable. FIG. 26A depicts end effector (2812) comprising upper jaw (2814) and lower jaw (2816). Upper jaw (2814) comprises body (2817) and placement tip (2819) extending distally from body (2817). Placement tip (2819) has a bent or angled configuration and comprises an underside surface (2822) that is flat. In this example, underside surface (2822) is also parallel with a top surface (2828) on nose portion (2826) of lower jaw (2816). In this manner, when end effector (2812) is closed and unloaded, underside surface (2822) can contact top surface (2828).

Figure 26B:
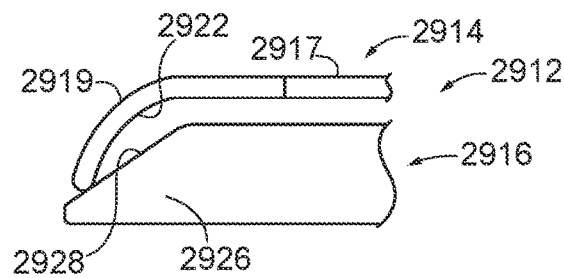
FIG. 26B depicts an enlarged side view of a distal portion of an alternative version of an end effector, with a placement tip of an upper jaw having an underside surface with a curved profile.

FIG. 26B depicts end effector (2912) comprising upper jaw (2914) and lower jaw (2916). Upper jaw (2914) comprises body (2917) and placement tip (2919) extending distally from body (2917). Placement tip (2919) has a curved configuration and comprises underside surface (2922) that is curved. Furthermore, lower jaw (2916) comprises nose portion (2926) with a tapered top surface (2928). The curvature of underside surface (2922) in combination with the tapered top surface (2928) of nose portion (2926) provides placement tip (2919) with point contact when end effector (2912) is closed and unloaded, as opposed to greater contact area as with end effector (2812) shown and described above.

Figure 26C:
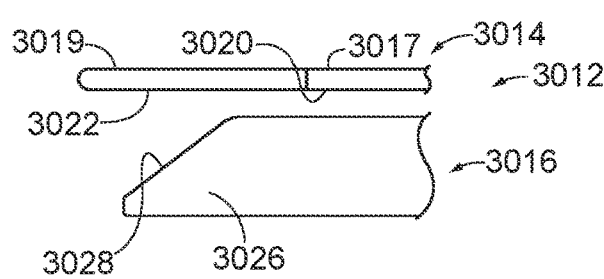
FIG. 26C depicts an enlarged side view of a distal portion of an alternative version of an end effector, with a straight placement tip of an upper jaw having an underside surface with a flat profile.

FIG. 26C depicts end effector (3012) comprising upper jaw (3014) and lower jaw (3016). Upper jaw (3014) comprises body (3017) and placement tip (3019) extending distally from body (3017). Placement tip (3019) has a straight configuration and comprises an underside surface (3022) that is straight. Placement tip (3019) is configured as elastically deformable as described above. In this manner, underside surface (3022) of placement tip (3019) extends along the same plane as an underside surface (3020) of body (3017) of upper jaw (3014). Furthermore, lower jaw (3016) comprises nose portion (3026) with a tapered top surface (3028). The straight configuration of underside surface (3022), in combination with the tapered top surface (3028) of nose portion (3026), eliminates placement tip (3019) contact with tapered top surface (3028) when end effector (3012) is closed and unloaded.

Figure 26D:
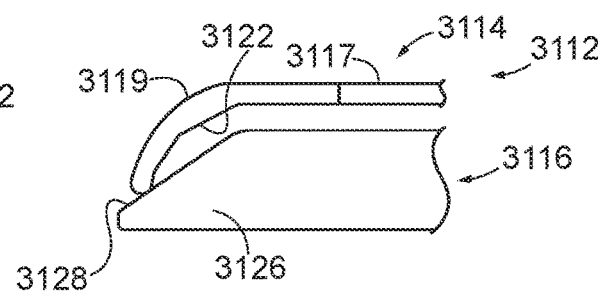
FIG. 26D depicts an enlarged side view of a distal portion of an alternative version of an end effector, with a placement tip of an upper jaw having an underside surface with a multi-angled profile.

FIG. 26D depicts end effector (3112) comprising upper jaw (3114) and lower jaw (3116). Upper jaw (3114) comprises body (3117) and placement tip (3119) extending distally from body (3117). Placement tip (3119) has a curved configuration and comprises an underside surface (3122) that is multi-angled. Placement tip (3119) is configured as elastically deformable as described above. Furthermore, lower jaw (3116) comprises nose portion (3126) with a tapered top surface (3128). The multi-angled nature of underside surface (3122) in combination with the tapered top surface (3128) of nose portion (3126) provides placement tip (3119) with point contact when end effector (3112) is closed and unloaded, as opposed to greater contact area as with end effector (3112) shown and described above.

Figure 26E:
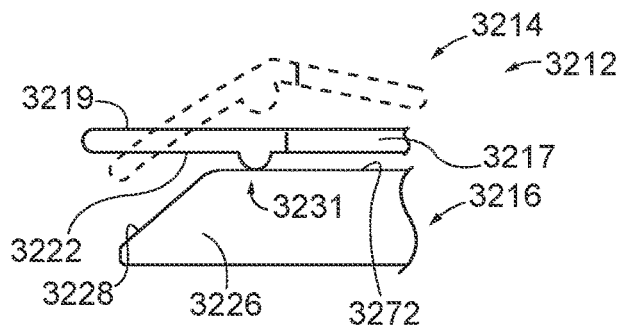
FIG. 26E depicts an enlarged side view of a distal portion of an alternative version of an end effector, with a placement tip of an upper jaw having an underside surface with a curved member and shown with the placement tip in dual positions.

FIG. 26E depicts end effector (3212) comprising upper jaw (3214) having dual positions and lower jaw (3216). Upper jaw (3214) comprises body (3217) and placement tip (3219) extending distally from body (3217). Placement tip (3219) has a bent or angled configuration when end effector (3212) is open and unloaded as shown in phantom in FIG. 26E. Placement tip (3219) comprises an underside surface (3222) that includes a curved protrusion (3231). Placement tip (3219) is configured as elastically deformable as described above. Furthermore, lower jaw (3216) comprises nose portion (3226) with a tapered top surface (3228) as well as deck (3272). The curved protrusion (3231) of underside surface (3222) of placement tip (3219) is configured to act as a pivot structure such that placement tip (3219) pivots from its bent or angled orientation shown in phantom to a straight, or at least less bent or angled, orientation in response to curved protrusion (3231) contacting a structure such as deck (3272) when end effector (3212) is closed and without tissue between jaws (3214, 3216), or tissue when end effector (3212) is closed and loaded with tissue between jaws (3214, 3216).

E. Exemplary Gaps

The various end effectors described herein provide visualization and guidance features as described above. Additionally, the ability of the placement tips to deflect or elastically deform can provide benefits in use during procedure where marching may be required or beneficial. In addition to the ability of the placement tips to elastically deform, the presence or absence of a gap between the placement tip and the opposite jaw's surface can impact visualization and marching. For instance, in some versions with little or no gap, the ability of the placement tip to elastically deform enables use of the end effector in marching procedures.

Figure 27A:
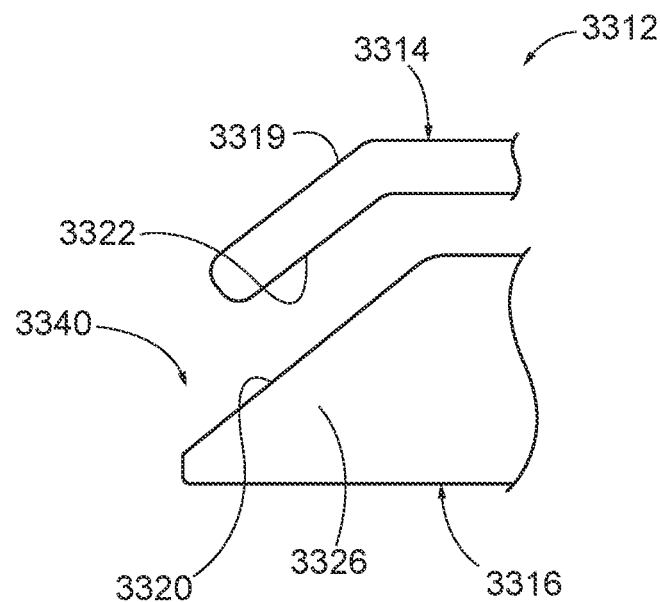
FIG. 27A depicts an enlarged side view of a distal portion of an alternative version of an end effector, showing a gap between a placement tip of an upper jaw and a nose portion of a lower jaw.
Figure 27B:
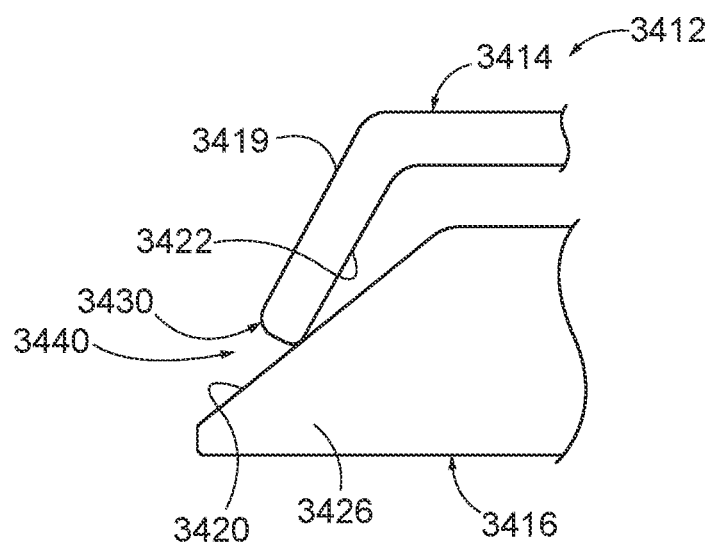
FIG. 27B depicts an enlarged side view of a distal portion of an alternative version of an end effector, showing a smaller gap between a distal end of a placement tip of an upper jaw and a nose portion of a lower jaw compared to the gap of FIG. 27A.

FIGS. 27A and 27B depict portions of end effectors that illustrate exemplary gaps and their configurations. FIG. 27A depicts an enlarged side view of a distal portion of an end effector (3312), showing a gap (3340) between a placement tip (3319) of an upper jaw (3314) and a nose portion (3326) of a lower jaw (3316). In the present example, end effector (3312) is shown in a closed and unloaded state. Placement tip (3319) comprises underside surface (3322) that is generally parallel with a top surface (3320) of nose portion (3326) of lower jaw (3316). In this manner, gap (3340) is generally of uniform size along underside surface (3322) of placement tip (3319) and top surface (3320) of nose portion (3326). With this configuration for gap (3340), and with the elastically deformable nature of placement tip (3319), end effector (3312) is configured for use in procedures where marching is desired.

FIG. 27B depicts an enlarged side view of a distal portion of an end effector (3412), showing a gap (3440) between a distal end (3430) of a placement tip (3419) of an upper jaw (3414) and a nose portion (3426) of a lower jaw (3416). Placement tip (3419) is bent or angled and with end effector (3412) closed and unloaded as shown, end (3430) contacts or nearly contacts a top surface (3420) of nose portion (3426) of lower jaw (3416). Thus in the present example, gap (3440) is either very small, or in the case where jaws (3414, 3416) touch, gap (3440) is absent altogether. In versions where gap (3440) is present, as shown gap (3440) increases in size as gap (3440) extends proximally. With this configuration, and with the elastically deformable nature of placement tip (3419), end effector (3412) is configured for use in procedures where marching is desired. In view of the teachings herein, other ways to configure end effectors with various gaps to aid in visualization, guidance, and marching will be apparent to those of ordinary skill in the art.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprises a body, a shaft extending from the body, wherein the shaft defines a longitudinal axis, and an end effector in communication with the shaft, wherein the end effector is operable to compress, staple, and cut tissue. The end effector comprises a pair of jaws, wherein at least one of the jaws is operable to move relative to the other jaw between an open position and a closed position, a cartridge configured to hold one or more staples, wherein the cartridge selectively connects with a first jaw of the pair of jaws, an anvil configured to be contacted by the one or more staples of the cartridge, wherein a second jaw of the pair of jaws comprises the anvil, and a placement tip that is elastically deformable. The placement tip extends distally from a select one of the pair of jaws, wherein the placement tip defines a first angle with respect to an axis of the select one of the jaws from which the placement tip extends when the end effector is in the open position, and a second angle with respect the axis of the select one of the jaws from which the placement tip extends when the end effector is in a closed position. The second angle differs from the first angle.

Example 2

The apparatus of Example 1, wherein the placement tip extends distally from the anvil.

Example 3

The apparatus of any one or more of Examples 1 through 2, wherein the second jaw comprising the anvil is movable relative to the first jaw.

Example 4

The apparatus of any one or more of Examples 1 through 3, wherein the placement tip comprises a shape selected from the group comprising straight, curved, bent, angled, and combinations thereof.

Example 5

The apparatus of any one or more of Examples 1 through 4, wherein the placement tip is configured such that deformation of the placement tip when the end effector is in the closed position causes an increase in the second angle relative to the first angle.

Example 6

The apparatus of any one or more of Examples 1 through 5, wherein the placement tip is configured such that deformation of the placement tip is caused by a clamping force applied to the placement tip when the end effector is in the closed position.

Example 7

The apparatus of any one or more of Examples 1 through 6, wherein the placement tip is configured such that the placement tip contacts a portion of the jaw opposite to the select one of the jaws from which the placement tip extends in response to a clamping force.

Example 8

The apparatus of any one or more of Examples 1 through 7, wherein the placement tip is configured such that the placement tip contacts tissue captured between the pair of jaws of the end effector in response to a clamping force.

Example 9

The apparatus of any one or more of Examples 1 through 8, wherein the placement tip comprises a distal end having a profile selected from the group comprising round, angled and pointed, toothed, flared, orb, asymmetric, and combinations thereof.

Example 10

The apparatus of any one or more of Examples 1 through 9, wherein the placement tip comprises distal sides defining a width profile selected from the group comprising angled, stepped, asymmetric, scalloped, bump-out, and combinations thereof.

Example 11

The apparatus of example 10, wherein the placement tip comprises a distal end having a profile selected from the group comprising round, angled and pointed, toothed, flared, orb, asymmetric, and combinations thereof.

Example 12

The apparatus of any one or more of Examples 1 through 11, wherein the placement tip comprises a multi-angled underside surface.

Example 13

The apparatus of any one or more of Examples 1 through 12, wherein the placement tip comprises an underside surface having a curved protrusion operably configured to move the placement tip from a first bent or angled position to a second straight or less bent or angled position in response to a clamping force applied to the placement tip.

Example 14

The apparatus of any one or more of Examples 1 through 13, wherein the placement tip comprises a distal end, wherein the distal end of the placement tip moves distally in response to a clamping force applied to the placement tip.

Example 15

The apparatus of any one or more of Examples 1 through 14, wherein the distal end of the placement tip moves away from the jaw opposite to the select one of the jaws from which the placement tip extends in response to the clamping force applied to the placement tip.

Example 16

An apparatus comprises a body, a shaft extending from the body, wherein the placement tip is configured such that the shaft defines a longitudinal axis, and an end effector in communication with the shaft, wherein the end effector is operable to compress, staple, and cut tissue. The end effector comprises a pair of jaws, wherein at least one of the jaws is operable to move relative to the other jaw between an open position and a closed position, a cartridge configured to hold one or more staples, wherein the cartridge selectively connects with a first jaw of the pair of jaws, an anvil configured to be contacted by the one or more staples of the cartridge, wherein a second jaw of the pair of jaws comprises the anvil, and a placement tip that is elastically deformable. The placement tip extends distally from a select one of the pair of jaws, wherein the placement tip defines a first angle with respect to a surface of a portion of the jaw opposite to the select one of the jaws from which the placement tip extends when the placement tip is in a first undeflected state, and a second angle with respect to the surface of the portion of the jaw opposite to the select one of the jaws from which the placement tip extends when the placement tip is in a second deflected state. The second angle differs from the first angle.

Example 17

The apparatus of Example 16, wherein the surface of the portion of the jaw opposite to the select one of the jaws from which the placement tip extends comprises a top surface of a nose portion of the cartridge, wherein the top surface is tapered.

Example 18

An apparatus comprises a body, a shaft extending from the body, wherein the shaft defines a longitudinal axis; an end effector in communication with the shaft, wherein the end effector is operable to compress, staple, and cut tissue. The end effector comprises a pair of jaws, wherein at least one of the jaws is operable to move relative to the other jaw between an open position and a closed position, a cartridge configured to hold one or more staples, wherein the cartridge selectively connects with a first jaw of the pair of jaws, an anvil configured to be contacted by the one or more staples of the cartridge, wherein a second jaw of the pair of jaws comprises the anvil, and a placement tip that is elastically deformable. The placement tip extends distally from a select one of the pair of jaws, wherein the placement tip comprises a distal end, wherein the placement tip is configured to transition from a first undeflected state to a second deflected state when the end effector is in the closed position and loaded. When the placement tip is in the first undeflected state the distal end of the placement tip is located proximal to a distal-most end of the jaw opposite to the select one of the jaws from which the placement tip extends, and when the placement tip is in the second deflected state the distal end of the placement tip is located distal to the distal-most end of the jaw opposite to the select one of the jaws from which the placement tip extends.

Example 19

The apparatus of Example 18, wherein the end effector defines a plurality of zones based on (a) a first plane defined by the distal-most end of the jaw opposite to the select one of the jaws from which the placement tip extends, (b) a second plane defined by a deck of the jaw opposite to the select one of the jaws from which the placement tip extends, wherein the first and second planes are orthogonal to each other, and (c) a third plane defined by a bottom surface of the jaw opposite to the select one of the jaws from which the placement tip extends, wherein the third and first plane are orthogonal to each other.

Example 20

The apparatus of Example 19, wherein the distal end of the placement tip is configured to move from one zone of the plurality of zones when the placement tip is in the first undeflected state to another zone of the plurality of zones when the placement tip is in the second deflected state.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. patent application Ser. No. 29/594,332, entitled "Surgical Stapler End Effector with Varying Deck Height and Tissue Gripping Features," filed Feb. 17, 2017, issued as U.S. Pat. No. D836,198 on Dec. 18, 2018, the disclosure of which is incorporated by reference herein. Various suitable ways in which the teachings herein may be combined with the teachings of U.S. patent application Ser. No. 29/594,332, issued as U.S. Pat. No. D836,198 on Dec. 18, 2018, will be apparent to those of ordinary skill in the art.

It should also be understood that the teachings herein may be readily combined with various teachings in U.S. patent application Ser. No. 29/594,335, issued as U.S. Pat. No. D833,010 on Nov. 6, 2018, entitled "Circular Surgical Stapler End Effector with Varying Deck Height and Tissue Gripping Features," filed Feb. 17, 2017, the disclosure of which is incorporated by reference herein. Various suitable ways in which the teachings herein may be combined with the teachings of U.S. patent application Ser. No. 29/594,335, issued as U.S. Pat. No. D833,010 on Nov. 6, 2018, will be apparent to those of ordinary skill in the art.

It should also be understood that the teachings herein may be readily combined with various teachings in U.S. patent application Ser. No. 15/435,607, entitled "Surgical Stapler with Insertable Distal Anvil Tip," filed Feb. 17, 2017, issued as U.S. Pat. No. 10,729,434 on Aug. 4, 2020, the disclosure of which is incorporated by reference herein. Various suitable ways in which the teachings herein may be combined with the teachings of U.S. patent application Ser. No. 15/435,607, issued as U.S. Pat. No. 10,729,434 on Aug. 4, 2020, will be apparent to those of ordinary skill in the art.

It should also be understood that the teachings herein may be readily combined with various teachings in U.S. patent application Ser. No. 15/435,618, entitled "Surgical Stapler with Cooperating Distal Tip Features on Anvil and Staple Cartridge," filed Feb. 17, 2017, issued as U.S. Pat. No. 10,806,451 on Oct. 20, 2020, the disclosure of which is incorporated by reference herein. Various suitable ways in which the teachings herein may be combined with the teachings of U.S. patent application Ser. No. 15/435,618, issued as U.S. Pat. No. 10,806,451 on Oct. 20, 2020, will be apparent to those of ordinary skill in the art.

It should also be understood that the teachings herein may be readily combined with various teachings in U.S. patent application Ser. No. 29/594,340, entitled "Surgical Stapler with Bent Anvil Tip and Angled Staple Cartridge Tip," filed Feb. 17, 2017, issued as U.S. Pat. No. D836,199 on Dec. 18, 2018, the disclosure of which is incorporated by reference herein. Various suitable ways in which the teachings herein may be combined with the teachings of U.S. patent application Ser. No. 29/594,340, issued as U.S. Pat. No. D836,199 on Dec. 18, 2018, will be apparent to those of ordinary skill in the art.

It should also be understood that the teachings herein may be readily combined with various teachings in U.S. patent application Ser. No. 15/435,631, entitled "Surgical Stapler with Bent Anvil Tip, Angled Staple Cartridge Tip, and Tissue Gripping Features," filed Feb. 17, 2017, issued as U.S. Pat. No. 10,758,231 on Sep. 1, 2020, the disclosure of which is incorporated by reference herein. Various suitable ways in which the teachings herein may be combined with the teachings of U.S. patent application Ser. No. 15/435,631, issued as U.S. Pat. No. 10,758,231 on Sep. 1, 2020, will be apparent to those of ordinary skill in the art.

It should also be understood that the teachings herein may be readily combined with various teachings in U.S. Patent No. 11,103,244, entitled "Surgical Stapling End Effector Jaw with Tip Deflecting Toward Other Jaw," filed on Jul. 16, 2018, and issued on Aug. 31, 2021, the disclosure of which is incorporated by reference herein. Various suitable ways in which the teachings herein may be combined with the teachings of U.S. Patent No. 11,103,244 will be apparent to those of ordinary skill in the art.

It should also be understood that the teachings herein may be readily combined with various teachings in U.S. Patent No. 11,272,930, entitled "Method of Surgical Stapling with End Effector Component Having a Curved Tip," filed on Jul. 16, 2018, and issued on Mar. 15, 2022, the disclosure of which is incorporated by reference herein. Various suitable ways in which the teachings herein may be combined with the teachings of U.S. Patent No. 11,272,930 will be apparent to those of ordinary skill in the art.

It should also be understood that the teachings herein may be readily combined with various teachings in U.S. Patent No. 10,973,515, entitled "Permanent Attachment Means for Curved Tip of Component of Surgical Stapling Instrument," filed on Jul. 16, 2018, and issued on Apr. 13, 2021, the disclosure of which is incorporated by reference herein. Various suitable ways in which the teachings herein may be combined with the teachings of U.S. Patent App. No. 10,973,515 will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S.

Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System, issued Sep. 30, 2014, the disclosure of which is incorporated by reference herein; U.S. Pat. No. 8,820,605, entitled "Robotically-Controlled Surgical Instrument with Force-Feedback Capabilities," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a first jaw having a plurality of staple apertures that house a plurality of staples;
   (b) a second jaw having a plurality of staple forming pockets configured to form the staples, wherein the first and second jaws are configured to transition from an open state to a closed state to clamp and staple tissue with the staples;
   (c) a tip coupled with one of the first and second jaws such that a proximal end of the tip is longitudinally constrained relative to the selected jaw, the tip comprising a body extending from the proximal end to a distal end; and
   wherein the distal end is moveable, via the application of a force external to the tip, from a first position, where the distal end is positioned at a first angle relative to the one of the first and second jaws, to a second position where the distal end is positioned at and a second angle, different from the first angle, relative to the one of the first and second jaws, wherein when the first and second jaws are in the closed state without tissue present between the first and second jaws and the distal end is in the first position, the distal end contacts the other of the first and second jaws.

2. The apparatus of claim 1, wherein the distal end is moveable about a range of angles relative to the one of the first and second jaws, including the first and second angles.

3. The apparatus of claim 2, wherein the external force is applied by the other of the first and second jaws as the first and second jaws are transitioned from the open to the closed state.

4. The apparatus of claim 2, wherein the external force is applied by presence of tissue between the first and second jaws as the first and second jaws are transitioned from the open to the closed state.

5. The apparatus of claim 2, wherein the range of angles is limited by the other of the first and second jaws.

6. The apparatus of claim 1, wherein the distal end returns to the first position upon cessation of the application of the external force.

7. The apparatus of claim 1, wherein the body is elastically deformable.

8. The apparatus of claim 1, wherein the proximal end of the body is affixed to a distal end of the one of the first and second jaws.

9. The apparatus of claim 1, wherein the body is spaced apart from a distal end of the other of the first and second jaws when the body is in at least one of the first and second positions.

10. The apparatus of claim 1, wherein the distal end is movable about an intermediate portion of the body distal to the proximal end and proximal to the distal end.

11. The apparatus of claim 1, wherein the intermediate portion is distal to a distal end of the other of the first and second jaws.

12. The apparatus of claim 1, wherein one of the first and second positions is configured for marching the first and second jaws through tissue.

13. A surgical instrument comprising a handle, a shaft having a proximal end coupled with handle and a distal end coupled with an end effector, the end effector comprising:
   (a) a first jaw configured to receive a staple cartridge having staples disposed therein;
   (b) a second jaw comprising an anvil including a plurality of staple forming pockets configured to form the staples, wherein the first and second jaws are pivotably coupled at a proximal end so as to be capable of transitioning between an open state and a closed state to clamp and staple tissue with the staples;
   (c) a tip coupled with the second jaw such that a proximal end of the tip is longitudinally constrained relative to the second jaw, the tip comprising a body extending from the proximal end to a distal end; and
   wherein the distal end is moveable, via the application of a force external to the tip, from a first position, where the distal end is positioned at a first angle relative to the one of the first and second jaws, to a second position where the distal end is positioned at a second angle, different from the first angle, relative to the one of the first and second jaws, wherein when the first and second jaws are in the closed state without tissue present between the first and second jaws and the distal end is in the first position, the distal end contacts the other of the first and second jaws.

14. The surgical instrument of claim 13, wherein the distal end is moveable about a range of angles relative to the one of the first and second jaws, including the first and second angles.

15. The surgical instrument of claim 14, wherein the external force is applied by the other of the first and second jaws as the first and second jaws are transitioned from the open to the closed state.

16. The surgical instrument of claim 14, wherein the external force is applied by presence of tissue between the first and second jaws as the first and second jaws are transitioned from the open to the closed state.

17. The surgical instrument of claim 14, wherein the range of angles is limited by the other of the first and second jaws.

18. The surgical instrument of claim 13, wherein the distal end returns to the first position upon cessation of the application of the external force.

19. The surgical instrument of claim 13, wherein the body is elastically deformable.

20. The surgical instrument of claim 13, wherein the proximal end of the body is affixed to a distal end of the one of the first and second jaws.

21. The surgical instrument of claim 13, wherein the body is spaced apart from a distal end of the other of the first and second jaws when the body is in at least one of the first and second positions.

22. The surgical instrument of claim 13, wherein the distal end is movable about an intermediate portion of the body distal to the proximal end and proximal to the distal end.

23. The surgical instrument of claim 13, wherein the intermediate portion is distal to a distal end of the other of the first and second jaws.

24. The surgical instrument of claim 13, wherein one of the first and second positions is configured for marching the first and second jaws through tissue.

25. An end effector for use with a handle or robotic am, the end effector comprising:
   (a) a first jaw configured to receive a staple cartridge having staples disposed therein;
   (b) a second jaw comprising an anvil including a plurality of staple forming pockets configured to form the staples, wherein the first and second jaws are pivotably coupled at a proximal end so as to be capable of transitioning between an open state and a closed state to clamp and staple tissue with the staples;
   (c) a tip coupled with the second jaw such that a proximal end of the tip is longitudinally constrained relative to the second jaw, the tip comprising a body extending from the proximal end to a distal end; and
   wherein the distal end is moveable, via the application of a force external to the tip, by one of the first jaw or tissue captured between the first and second jaws, about a range of angles relative to the second jaw, including a first angle relative to the second jaw and a second angle, different from the first angle, relative to the second jaw, wherein one of the first and second angles is configured for marching the first and second jaws through tissue, wherein when the first and second jaws are in the closed state without tissue present between the first and second jaws and the distal end is at the first angle, the distal end contacts the other of the first and second jaws.

\* \* \* \* \*